(12) United States Patent
Mueller et al.

(10) Patent No.: US 9,284,564 B2
(45) Date of Patent: Mar. 15, 2016

(54) RECOMBINANT MICROORGANISMS COMPRISING STEREOSPECIFIC DIOL DEHYDRATASE ENZYME AND METHODS RELATED THERETO

(71) Applicant: LanzaTech New Zealand Limited, Auckland (NZ)

(72) Inventors: Alexander Paul Mueller, Auckland (NZ); Michael Koepke, Auckland (NZ)

(73) Assignee: LanzaTech New Zealand Limited, Auckland (NZ)

(*) Notice: Subject to any disclaimer, the term of this patent is extended or adjusted under 35 U.S.C. 154(b) by 189 days.

(21) Appl. No.: 14/011,872

(22) Filed: Aug. 28, 2013

(65) Prior Publication Data

US 2014/0065698 A1 Mar. 6, 2014

Related U.S. Application Data

(60) Provisional application No. 61/694,104, filed on Aug. 28, 2012, provisional application No. 61/720,224, filed on Oct. 30, 2012.

(51) Int. Cl.
| | |
|---|---|
| C12N 15/70 | (2006.01) |
| C12P 7/04 | (2006.01) |
| C12P 7/28 | (2006.01) |
| C12P 7/24 | (2006.01) |
| C12P 41/00 | (2006.01) |
| C12N 1/21 | (2006.01) |
| C12N 1/15 | (2006.01) |
| C12N 5/10 | (2006.01) |
| C12N 9/88 | (2006.01) |

(52) U.S. Cl.
CPC ........ *C12N 15/70* (2013.01); *C12N 9/88* (2013.01); *C12P 7/04* (2013.01); *C12P 7/24* (2013.01); *C12P 7/28* (2013.01); *C12P 41/002* (2013.01); *C12Y 402/01028* (2013.01)

(58) Field of Classification Search
None
See application file for complete search history.

(56) References Cited

U.S. PATENT DOCUMENTS

| | | | |
|---|---|---|---|
| 5,173,429 A | 12/1992 | Gaddy | |
| 5,593,886 A | 1/1997 | Gaddy | |
| 6,368,819 B1 | 4/2002 | Gaddy | |
| 7,629,161 B2 | 12/2009 | Laffend et al. | |
| 2007/0292927 A1* | 12/2007 | Donaldson et al. | 435/160 |
| 2011/0229947 A1 | 9/2011 | Zahn et al. | |
| 2011/0269215 A1 | 11/2011 | Yoshikuni et al. | |
| 2012/0196341 A1 | 8/2012 | Donaldson et al. | |
| 2012/0252083 A1 | 10/2012 | Koepke et al. | |
| 2013/0224838 A1 | 8/2013 | Koepke et al. | |

FOREIGN PATENT DOCUMENTS

| | | |
|---|---|---|
| WO | WO 02/08438 | 1/2002 |
| WO | WO 2008/028055 | 3/2008 |
| WO | WO2011 022651 | 2/2011 |
| WO | WO2011032934 | 3/2011 |
| WO | WO2012 024522 | 2/2012 |
| WO | WO2012/053905 | 4/2012 |
| WO | 2013/185123 A1 | 12/2013 |

OTHER PUBLICATIONS

Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Jain et al., Microbial Cell Factories 10:97, published Nov. 10, 2011.*
Wikipedia, article titled "Origin of replication", downloaded Jul. 24, 2015.*
Bochovchin et al., Biochemistry 16(6):1082-1092, 1977.*
Weidner et al., Journal of Bacteriology 178(8):2440-2444, 1996.*
Kopke et al., GenBank accession No. YP_003779353, Jul. 19, 2010.*
Kopke et al., GenBank accession No. YP_003779354, Jul. 19, 2010.*
Kopke et al., GenBank accession No. CP001666, Jul. 12, 2010.*
Tabor et al., PNAS 82:1074-1078, 1985.*
Tabor, S., Current Protocols in Molecular Biology, pp. 12.2.1-12.2.11, Greene/Wiley-Interscience, New York, 1990.*
George, H a, J L Johnson, W E Moore, L V Holdeman, and J S Chen. 1983. "Acetone, Isopropanol, and Butanol Production by Clostridium beijerinckii (syn. Clostridium butylicum) and Clostridium aurantibutyricum." Applied and environmental microbiology 45(3): 1160-3.
Hazelwood, Lucie A, Jean-Marc Daran, Antonius J A van Maris, Jack T Pronk, and J Richard Dickinson. 2008. "The Ehrlich pathway for fusel alcohol production: a century of research on *Saccharomyces cerevisiae* metabolism." Applied and environmental microbiology 74(8): 2259-66. (Jul. 15, 2012).
Munasinghe, Pradeep Chaminda, and Samir Kumar Khanal. 2010. "Biomass-derived syngas fermentation into biofuels: Opportunities and challenges." Bioresource technology 101(13): 5013-22. (Jul. 16, 2011).
Ramachandriya, Karthikeyan D, Mark R Wilkins, Marthah J M Delorme, Xiaoguang Zhu, Dimple K Kundiyana, Hasan K Atiyeh, and Raymond L Huhnke. 2011. "Reduction of acetone to isopropanol using producer gas fermenting microbes." Biotechnology and bioengineering 108(10): 2330-2338. (Sep. 4, 2011).
Berrios-Rivera, Susana J, Ka-Yiu San, and George N Bennett. 2003. "The effect of carbon sources and lactate dehydrogenase deletion on 1,2-propanediol production in *Escherichia coli*." Journal of industrial microbiology & biotechnology 30(1): 34-40. 4 (May 24, 2012).

(Continued)

*Primary Examiner* — Delia Ramirez
(74) *Attorney, Agent, or Firm* — Andrea E. Schoen

(57) ABSTRACT

A stereospecific enzyme in *C. autoethanogenum* permits the conversion of racemic propanediol to acetone and/or propionaldehyde. Entantiomeric starting materials lead to different products. If desired, the products may be reduced to form alcohols. The reaction can be performed in various host cells, so that various materials may be used as carbon and/or energy sources.

19 Claims, 8 Drawing Sheets

(56) References Cited

OTHER PUBLICATIONS

Jain, Rachit, and Yajun Yan. 2011. "Dehydratase mediated 1-propanol production in metabolically engineered *Escherichia coli*." Microbial cell factories 10(1): 97. (Mar. 10, 2012).
van Leeuwen, Bianca N M, Albertus M van der Wulp, Isabelle Duijnstee, Antonius J a van Maris, and Adrie J J Straathof. 2012. "Fermentative production of isobutene." Applied microbiology and biotechnology 93(4): 1377-87. (Mar. 7, 2012).
Abrini, Jamal, Henry Naveau, and E.J. Nyns. 1994. "*Clostridium autoethanogenum*, sp. nov., an anaerobic bacterium that produces ethanol from carbon monoxide." Archives of microbiology 161(4): 345-351. (Sep. 4, 2011).
Tanner, Ralph S., L.M. Miller, and Decheng Yang. 1993. "*Clostridium ljungdahlii* sp. nov., an acetogenic species in clostridial rRNA homology group I." International journal of systematic bacteriology 43(2): 232. (Sep. 4, 2011).
Tyurin, Michael, and Michael Kiriukhin. 2012. "Electrofusion of cells of Acetogen *Clostridium* sp. MT 351 with erm (B) or cat in the chromosome." Journal of Biotech: 1-12. (May 31, 2012).
Tirado-Acevedo O. Production of Bioethanol from Synthesis Gas Using Clostridium ljungdahlii. PhD thesis, North Carolina State University, 2010.
Köpke, Michael, Christophe Mihalcea, Fungmin Liew, Joseph H Tizard, Mohammed S Ali, Joshua J Conolly, Bakir Al-Sinawi, and Séan D Simpson. 2011. "2,3-Butanediol Production by Acetogenic Bacteria, an Alternative Route to Chemical Synthesis, Using Industrial Waste Gas." Applied and environmental microbiology 77(15): 5467-75. 8 (Sep. 4, 2011).
Murray, N.E. et al. (2000) Microbial. Molec. Biol. Rev. 64, 412.
Köpke, Michael, Claudia Held, Sandra Hujer, Heiko Liesegang, Arnim Wiezer, Antje Wollherr, Armin Ehrenreich, Wolfgang Liebl, Gerhard Gottschalk, and Peter Dürre. 2010. "Clostridium ljungdahlii represents a microbial production platform based on syngas." Proceedings of the National Academy of Sciences of the United States of America 107 (29): 13087-92. (Jul. 27, 2011).
Schiel-Bengelsdorf, Bettina, and Peter Dürre. 2012. "Pathway engineering and synthetic biology using acetogens." FEBS Letters (May). (May 8, 2012).
Strätz, M, U Sauer, a Kuhn, and P Dürre. 1994. "Plasmid Transfer into the Homoacetogen Acetobacterium woodii by Electroporation and Conjugation." Applied and environmental microbiology 60(3): 1033-7.
Mermelstein et al., 1992, Biotechnology, 10, 190-195.
Jennert et al., 2000, Microbiology, 146: 3071-3080.
Tyurin et al., 2004, Appl. Environ. Microbiol. 70: 883-890.
Prasanna Tamarapu Parthasarathy, 2010, Development of a Genetic Modification System in Clostridium scatologenes ATCC 25775 for Generation of Mutants, Masters Project Western Kentucky University.
Herbert et al., 2003, FEMS Microbiol. Lett. 229: 103-110.
Williams et al., 1990, J. Gen. Microbiol. 136: 819-826.
Toraya T, Shirakashi T, Kosuga T, Fukui S. 1976. "Substrate Specificity of Coenzyme B12-Dependent Diol Dehydratase." Biochemical and biophysical research communications 69(2): 475-480.
Brien, Jessica Rae O, Celine Raynaud, Christian Croux, Laurence Girbal, Philippe Soucaille, and William N Lanzilotta. 2004. "Insight into the Mechanism of the B 12 -Independent Glycerol Dehydratase from Clostridium butyricum: Preliminary Biochemical and Structural Characterization ±" Biochemistry 43(16): 4636-4645.
Ismaiel, a a, C X Zhu, G D Colby, and J S Chen. 1993. "Purification and characterization of a primary-secondary alcohol dehydrogenase from two strains of Clostridium beijerinckii." Journal of bacteriology 175(16): 5097-105.

* cited by examiner

RECOMBINANT MICROORGANISMS COMPRISING STEREOSPECIFIC DIOL DEHYDRATASE ENZYME AND METHODS RELATED THERETO

FIELD OF THE INVENTION

The present invention relates to a enzymatic reaction converting propane-1,2-diol to propan-2-one and propanal and a process to produce products including propanal, propan-2-one, propan-1-ol and/or propan-2-ol by microbial fermentation of a substrate.

BACKGROUND OF THE INVENTION

To date, most chemicals such as propanal, propan-2-one, propan-1-ol and/or propan-2-ol, propylene, or isubutylene are derived from petrochemical sources. With diminishing global reserves of crude oil and increasing demand from developing countries, the pressure on oil supply and demand will grow and alternative bio-based chemicals are being developed. The current generation of biochemicals that use either food or non-food crops to produce sugar or cellulose-based feedstocks may have drawbacks relating to land-use, food-security, and volatility of supply and environmental issues.

Propan-2-one is an important solvent with an annual demand of 2 million metric tonns per annum in the United States. Propan-2-ol is used as solvent for coatings or for industrial processes with a capacity of 3 million metric tonns per annum. 1-propanol is important in production of drugs and cosmetics and is considered as fuel substitute. Isobutylene is a chemical building block and key precursor for numerous chemicals. The worldwide demand for isobutylene has been estimated to exceed 10 million metric tons per year and its market value at 25 billion US dollar.

It has long been recognised that catalytic processes may be used to convert gases consisting primarily of CO and/or CO and hydrogen ($H_2$) into a variety of fuels and chemicals. However, micro-organisms may also be used to convert these gases into fuels and chemicals. These biological processes, although generally slower than chemical reactions, have several advantages over catalytic processes, including higher specificity, higher yields, lower energy costs and greater resistance to poisoning.

CO is a major free energy-rich by-product of the incomplete combustion of organic materials such as coal or oil and oil derived products. For example, the steel industry in Australia is reported to produce and release into the atmosphere over 500,000 tonnes of CO annually.

The ability of micro-organisms to grow on CO as their sole carbon source is a property of organisms that use the acetyl coenzyme A (acetyl CoA) biochemical pathway of autotrophic growth (also known as the Woods-Ljungdahl pathway). A large number of anaerobic organisms including carboxydotrophic, photosynthetic, methanogenic and acetogenic organisms have been shown to metabolize CO to various end products, namely $CO_2$, $H_2$, methane, n-butanol, acetate and ethanol. When using CO as the sole carbon source all such organisms produce at least two of these end products.

Some microorganisms such as *Clostridium acetobutylicum* or *Clostridium beijerinckii* are known to produce propan-2-one or propan-2-ol as major by-products during butanol fermentation (ABE or IBE fermentation) (George et al. 1983), while propan-1-ol is a byproduct of fermentations with yeast *Saccharomyces cerevisiae* (Hazelwood et al. 2008). However, all these organisms rely on sugar or starch based substrates. Acetogenic organisms such as the closely related microorganisms *Clostridium autoethanogenum*, *C. ljungdahlii*, and *C. ragsdalei* are able to grow chemoautotrophically on CO or $CO_2/H_2$ containing gases as sole energy and carbon source and synthesize products such as acetate, ethanol, butanol or 2,3-butanediol, but neither propan-2-one nor propan-2-ol (Munasinghe and Khanal 2010). Although propan-2-one to propan-2-ol reduction have been shown in acetogenic species, the underlying principle is unknown (Ramachandriya et al. 2011).

It is an object of the invention to provide a method of production of propanal, propan-2-one, propan-1-ol and/or propan-2-ol or their precursors.

SUMMARY OF INVENTION

The invention provides, inter alia, an enzymatic reaction converting propane-1,2-diol to propan-2-one and propanal and methods for the production of propanal, propan-2-one, propan-1-ol and/or propan-2-ol by microbial fermentation (in particular of a substrate comprising CO), and recombinant microorganisms of use in such methods.

In a first aspect, the invention provides an enzymatic reaction converting propane-1,2-diol to propan-2-one and propanal catalysed by a type of diol dehydratase enzyme.

In one particular embodiment, a method of producing propanal, propan-2-one, propan-1-ol and/or propan-2-ol comprising fermenting a substrate in the presence of a microorganism wherein the substrate contains propane-1,2-diol is provided.

In one particular embodiment, the microorganism produces one or more other products. In one embodiment, the one or more other products is ethanol, butanol and/or butanediol.

In one embodiment, the microorganism is a carboxydotrophic microorganism.

In one particular embodiment, the carboxydotrophic microorganism is *Clostridium autoethanogenum*, *Clostridium ljungdahlii*, *Clostridium ragsdalei*, *Clostridium carboxidivorans*, *Clostridium drakei*, *Clostridium scatologenes*, *Clostridium aceticum*, *Clostridium formicoaceticum*, *Clostridium magnum*, *Butyribacterium methylotrophicum*, *Acetobacterium woodii*, *Alkalibaculum bacchii*, *Blautia producta*, *Eubacterium limosum*, *Moorella thermoacetica*, *Moorella thermautotrophica*, *Sporomusa ovata*, *Sporomusa silvacetica*, *Sporomusa sphaeroides*, *Oxobacter pfennigii*, and *Thermoanaerobacter kiuvi*.

In one embodiment, the microorganism is a recombinant microorganism as defined hereinafter.

In one embodiment, the microorganism is selected from the genus *Escherichia*, *Saccharomyces*, *Clostridium*, *Bacillus*, *Lactococcus*, *Zymomonas*, *Corynebacterium*, *Pichia*, *Candida*, *Hansenula*, *Trichoderma*, *Acetobacterium*, *Ralstonia*, *Cupravidor Salmonella*, *Klebsiella*, *Paenibacillus*, *Pseudomonas*, *Lactobacillus*, *Rhodococcus*, *Enterococcus*, *Alkaligenes*, *Brevibacterium*, *Methylobacterium*, *Methylococcus*, *Methylomonas*, *Methylocystis*, *Methylosinus*.

In one particular embodiment, the microorganism is selected from the group consisting of *E. coli*, *Saccharomyces cerevisiae*, *Clostridium acetobutylicum*, *C. beijerinckii*, *C. saccharbutyricum*, *C. saccharoperbutylacetonicum*, *C. butyricum*, *C. diolis*, *C. kluyveri*, *C. pasterianium*, *C. novyi*, *C. difficile*, *C. thermocellum*, *C. cellulolyticum*, *C. cellulovorans*, *C. phytofermentans*, *Lactococcus lactis*, *Bacillus subtilis*, *Bacillus licheniformis*, *Zymomonas mobilis*, *Klebsiella oxytoca*, *Klebsiella pneumonia*, *Corynebacterium glutamicum*, *Trichoderma reesei*, *Ralstonia eutropha*,

*Cupriavidus necator Pseudomonas putida, Lactobacillus plantarum, Methylobacterium extorquens.*

In one embodiment the method comprises the steps of:
a. aerobic or anaerobic fermentation providing a substrate comprising of sugar, starch, cellulose, biomass hydrolisates, syngas and/or glycerol to a bioreactor containing a substrate comprising a culture of one or more microorganisms;
b. providing propane-1,2-diol to the substrate; and
c. anaerobically fermenting the culture in the bioreactor to produce propanal, propan-2-one, propan-1-ol and/or propan-2-ol.

In one particular embodiment the method comprises the steps of:
a. providing a substrate comprising CO to a bioreactor containing a substrate comprising a culture of one or more carboxydotrophic microorganisms;
b. providing propane-1,2-diol to the substrate; and
c. anaerobically fermenting the culture in the bioreactor to produce propanal, propan-2-one, propan-1-ol and/or propan-2-ol.

In one particular embodiment the method comprises the steps of:
a. capturing CO-containing gas produced as a result of an industrial process
b. anaerobic fermentation of the CO-containing gas to produce propanal, propan-2-one, propan-1-ol and/or propan-2-ol in a substrate comprising one or more carboxydotrophic microorganisms and propane-1,2-diol.

In one embodiment the method comprises the steps of:
a. aerobic or anaerobic fermentation providing a substrate comprising of sugar, starch, cellulose, biomass hydrolisates, syngas and/or glycerol to a bioreactor containing a substrate comprising a culture of one or more microorganisms;
b. with one or more microorganisms producing propane-1, 2-diol;
c. and one or more microrganisms convert propane-1,2-diol and produce propanal, propan-2-one, propan-1-ol and/or propan-2-ol.

In particular embodiments of the method aspects, the fermentation occurs in an aqueous culture medium.

In one embodiment, the propane-1,2-diol is (R)-propane-1,2-diol and the product is propan-2-one and/or propan-2-ol.

In one embodiment, the propane-1,2-diol is (S)-propane-1,2-diol and the product is propanal and/or propan-1-ol.

Preferably, the substrate comprises CO. Preferably, the substrate is a gaseous substrate comprising CO. In one embodiment, the substrate comprises an industrial waste gas. In certain embodiments, the gas is steel mill waste gas or syngas.

In one embodiment, the substrate will typically contain a major proportion of CO, such as at least about 20% to about 100% CO by volume, from 20% to 70% CO by volume, from 30% to 60% CO by volume, and from 40% to 55% CO by volume. In particular embodiments, the substrate comprises about 25%, or about 30%, or about 35%, or about 40%, or about 45%, or about 50% CO, or about 55% CO, or about 60% CO by volume.

In one embodiment, the method further comprises the step of recovering the propanal, propan-2-one, propan-1-ol and/or propan-2-ol and optionally one or more other products from the fermentation broth.

In one embodiment, the propane-1,2-diol is added to the fermentation substrate prior to, concurrently with, or subsequently to the introduction of the microorganism to the substrate.

In one embodiment, the CO and/or other components of a fermentation broth may be added to the substrate prior to, concurrently with, or subsequently to the introduction of the propane-1,2-diol.

In one embodiment, the propane-1,2-diol present in the substrate is produced by the carboxydotrophic microorganism that produces the propanal, propan-2-one, propan-1-ol and/or propan-2-ol. In one embodiment, the propane-1,2-diol may be produced in the same bioreactor or a different bioreactor.

In a further embodiment, the propane-1,2-diol is produced by a different microorganism in the same bioreactor or in a different bioreactor.

Recombinant Microorganisms

In a second aspect, the invention provides a recombinant microorganism modified to express one or more exogenous diol dehydratase enzymes not present in a parental microorganism (may be referred to herein as an exogenous enzyme).

In third aspect, the invention provides a microorganism modified to over-express one or more endogenous diol dehydratase enzymes which are present in a parental microorganism (may be referred to herein as an endogenous enzyme).

In forth aspect, the invention provides a microorganism modified to express variants of one or more endogenous diol dehydratase enzymes which are present in a parental microorganism (may be referred to herein as an endogenous enzyme).

In an embodiment of the second, third or fourth aspects, the microorganism is adapted to be able to achieve a higher yield of propanal, propan-2-one, propan-1-ol and/or propan-2-ol than would be produced by a parental microorganism.

In an embodiment of the second, third or fourth aspects, the microorganism is adapted to produce propanal, propan-2-one, propan-1-ol and/or propan-2-ol at a faster rate than would be produced by a parental microorganism.

In one embodiment of the second aspect, the diol dehydratase enzyme.

In a particular embodiment, the diol dehydratase enzyme has the identifying characteristics of a diol dehydratase from *Clostridium autoethanogenum* or *C. ljungdahlii* (EC 4.1.2.28), or a functionally equivalent variant thereof.

In a particular embodiment, the diol dehydratase enzyme has the identifying characteristics of a propanediol dehydratase from *Klebsiella oxytoca* or *K. pneumoniae* (EC 4.1.2.30), or a functionally equivalent variant thereof.

In one embodiment of the second aspect, the novel diol dehydratase enzyme and activase enzyme are as defined in SEQ ID NO: 1 and 2 (enzyme of *C. autoethanogenum*) and YP_003779353 and YP_003779354 (enzyme of *C. ljungdahlii*), or a functionally equivalent variant thereof.

In one embodiment of the second aspect, the novel diol dehydratase enzyme and its activase enzyme are encoded by a nucleic acid sequence as defined in SEQ ID NO: 3 and 4 (genes from *C. autoethanogenum*) and CLJU_c11830; 9444800 and CLJU_c11831; 9444801 (genes of *C. ljungdahlii*), or a functionally equivalent variant thereof.

In one embodiment of the third aspect, the three subunit comprising diol dehydratase enzyme of *Klebsiella* as defined in YP_002236780, YP_002236781, YP_002236782 (*K. pneumonia*) and 1DIO_A, 1DIO_B, 1DIO_C (*K. oxytoca*), or a functionally equivalent variant thereof.

In one embodiment of the third aspect, the three diol dehydratase enzyme subunits of *Klebsiella* are encoded by a nucleic acids as defined in GI:206575748, GI:206575749, GI:206575750 (*K. pneumonia*) and GI:868006, GI:868007, GI:868008 (*K. oxytoca*), or a functionally equivalent variant thereof.

In a particular embodiment of the second or third aspects, the recombinant microorganism is modified such that expression of an endogenous enzyme is attenuated, or is knocked-out relative to the expression of the same enzyme in the parental microorganism.

In one embodiment, the enzyme whose expression is attenuated or is knocked out is an alcohol dehydrogenase enzyme. In particular embodiments, the secondary alcohol dehydrogenase enzyme is defined in SEQ ID NO: 5 (*C. autoethanogenum*) and ADK15544.1 (*C. ljungdahlii*), or is a functionally equivalent variant thereof. In further embodiments, the secondary alcohol dehydrogenase enzyme is encoded by a nucleic acid as defined in SEQ ID NO: 6. (*C. autoethanogenum*) and CLJU_c24860; GI:300435777 (*C. ljungdahlii*).

In a further embodiment, the recombinant organism produces propanal and/or propan-2-one in addition to, or instead of propan-1-ol and/or propan-2-ol.

In one embodiment, the microorganism comprises one or more exogenous nucleic acids adapted to increase expression of one or more endogenous nucleic acids and which one or more endogenous nucleic acids encode a diol dehydratase referred to hereinbefore.

In one embodiment, the one or more exogenous nucleic acids adapted to increase expression is a regulatory element. In one embodiment, the regulatory element is a promoter. In one embodiment, the promoter is a constitutive promoter. In one embodiment, the promoter is selected from the group comprising Wood-Ljungdahl gene cluster, a pyruvate:ferredoxin oxidoreductase promoter, an Rnf complex operon promoter, ATP synthase operon promoter and Phosphotransacetylase/Acetate kinase operon promoters.

In one embodiment, the recombinant microorganism is further adapted to express one or more exogenous enzymes to produce propane-1,2-diol including but not limited to methylglyoxal synthase (mgsA); methylglyoxal reductase (ydjG); secondary alcohol dehydrogenase (gldA/budC); lactaldehyde reductase/primary alcohol dehydrogenase (fucO). In a further aspect, the microorganism is adapted to over-express one or more endogenous enzymes in the propane-1,2-diol biosynthesis pathway.

In one embodiment, the one or more exogenous nucleic acids is a nucleic acid construct or vector, in one particular embodiment a plasmid, encoding a diol dehydratase enzyme referred to hereinbefore.

In one embodiment, the exogenous nucleic acid is an expression plasmid.

In one particular embodiment, the parental microorganism is selected from the group of carboxydotrophic bacteria comprising *Clostridium autoethanogenum*, *Clostridium ljungdahlii*, *Clostridium ragsdalei*, *Clostridium carboxidivorans*, *Clostridium drakei*, *Clostridium scatologenes*, *Clostridium aceticum*, *Clostridium formicoaceticum*, *Clostridium magnum*, *Butyribacterium methylotrophicum*, *Acetobacterium woodii*, *Alkalibaculum bacchii*, *Blautia producta*, *Eubacterium limosum*, *Moorella thermoacetica*, *Moorella thermautotrophica*, *Sporomusa ovata*, *Sporomusa silvacetica*, *Sporomusa sphaeroides*, *Oxobacter pfennigii*, and *Thermoanaerobacter kiuvi*.

In one embodiment the parental microorganism is *Clostridium autoethanogenum* or *Clostridium ljungdahlii*. In one particular embodiment, the microorganism is *Clostridium autoethanogenum* DSM23693 a derivate of strain DSM10061. In another particular embodiment, the microorganism is *Clostridium ljungdahlii* DSM13528 (or ATCC55383).

In one embodiment the parental microorganism is *Escherichia coli* or *Lactococcus lactis*.

Isolated Nucleic Acid (from *C. Autoethanogenum* and *C. Ljungdahlii*)

In a fourth aspect, the invention provides a nucleic acid encoding a diol dehydratase wherein the nucleic acid is isolated from a carboxydotrophic microorganism.

In a further embodiment of the fourth aspect, the carboxydotrophic microorganism is *Clostridium autoethanogenum* or *Clostridium ljungdahlii*. In one particular embodiment, the microorganism is *Clostridium autoethanogenum* DSM23693 a derivate of strain DSM10061. *C. autoethanogenum*.

In a further embodiment of the fourth aspect, when expressed in a microorganism, the nucleic acid encoding a diol dehydratase facilitates an increased yield and/or rate of production of propanal, propan-2-one, propan-1-ol and/or propan-2-ol by fermentation of a substrate comprising CO and propane-1,2-diol.

In one embodiment of the fourth aspect, the nucleic acid encoding a diol dehydratase is SEQ ID NO:1 and 2 or is a functionally equivalent variant thereof.

In one embodiment, the nucleic acid comprises sequences encoding one or more of the enzymes of the invention defined herein before which when expressed in a microorganism allows the microorganism to produce propanal, propan-2-one, propan-1-ol and/or propan-2-ol by fermentation of a substrate comprising CO and propane-1,2-diol. In one particular embodiment, the invention provides a nucleic acid encoding two enzymes which when expressed in a microorganism allows the microorganism to produce propanal, propan-2-one, propan-1-ol and/or propan-2-ol by fermentation of a substrate comprising CO.

In one embodiment, the nucleic acids of the invention further comprise a promoter. In one embodiment, the promoter allows for constitutive expression of the genes under its control. In a particular embodiment a Wood-Ljungdahl cluster promoter is used. In other particular embodiments a pyruvate:ferredoxin oxidoreductase promoter, an Rnf complex operon promoter, ATP synthase operon promoter or a Phosphotransacetylase/Acetate kinase operon promoter is used. In one particular embodiment, the promoter is from *C. autoethanogenum*.

In a fifth aspect, the invention provides a nucleic acid construct or vector comprising one or more nucleic acids of the fourth aspect.

In one particular embodiment, the nucleic acid construct or vector is an expression construct or vector. In one particular embodiment, the expression construct or vector is a plasmid.

In a sixth aspect, the invention provides a host organism comprising any one or more of the nucleic acids of the fourth aspect or vectors or constructs of the fifth aspect.

In a seventh aspect, the invention provides a composition comprising an expression construct or vector as referred to in the fourth aspect of the invention and a methylation construct or vector.

Preferably, the composition is able to produce a recombinant microorganism according to the second aspect of the invention.

In one particular embodiment, the expression construct/vector and/or the methylation construct/vector is a plasmid.

In an eighth aspect, the invention provides propan-1-ol, propan-2-ol, propanal and/or propan-2-one when produced by the method of the first aspect.

In another aspect, the invention provides a method for the production of a microorganism of the second or third aspect of the invention comprising transforming a carboxydotrophic acetogenic parental microorganism by introduction of one or more nucleic acids such that the microorganism is capable of producing propanal, propan-2-one, propan-1-ol and/or propan-2-ol, or producing an increased amount of propanal, propan-2-one, propan-1-ol and/or propan-2-ol compared to the parental microorganism, and optionally one or more other products by fermentation of a substrate comprising CO and propane-1-2-diol, wherein the parental microorganism is not capable of producing propanal, propan-2-one, propan-1-ol and/or propan-2-ol, or produces propanal, propan-2-one, propan-1-ol and/or propan-2-ol at a lower level than the recombinant microorganism, by fermentation of a substrate comprising CO.

In one particular embodiment, a parental microorganism is transformed by introducing one or more exogenous nucleic acids adapted to express one or more enzymes for biosynthesis of propane-1,2-diol including but not limited to methylglyoxal synthase (mgsA); methylglyoxal reductase (ydjG); secondary alcohol dehydrogenase (gldA/budC); lactaldehyde reductase/primary alcohol dehydrogenase (fucO). In a further embodiment, a parental microorganism is further transformed by introducing one or more exogenous nucleic acids adapted to express one or more enzyme in the propane-1,2-diol biosynthesis pathway. In a further embodiment, a parental microorganism is further transformed by expressing or overexpressing one or more endogenous nucleic acids adapted to express one or more enzyme in the propane-1,2-diol biosynthesis pathway. In one embodiment, a parental microorganism is transformed with one or more nucleic acids adapted to over-express one or more endogenous enzymes in the propane-1,2-diol pathway which are naturally present in the parental microorganism.

In certain embodiments, the one or more enzymes are as herein before described.

The invention may also be said broadly to consist in the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

BRIEF DESCRIPTION OF THE FIGURES

These and other aspects of the present invention, which should be considered in all its aspects, will become apparent from the following description, which is given by way of example only, with reference to the accompanying figures.

DETAILED DESCRIPTION OF THE INVENTION

Figure 1:
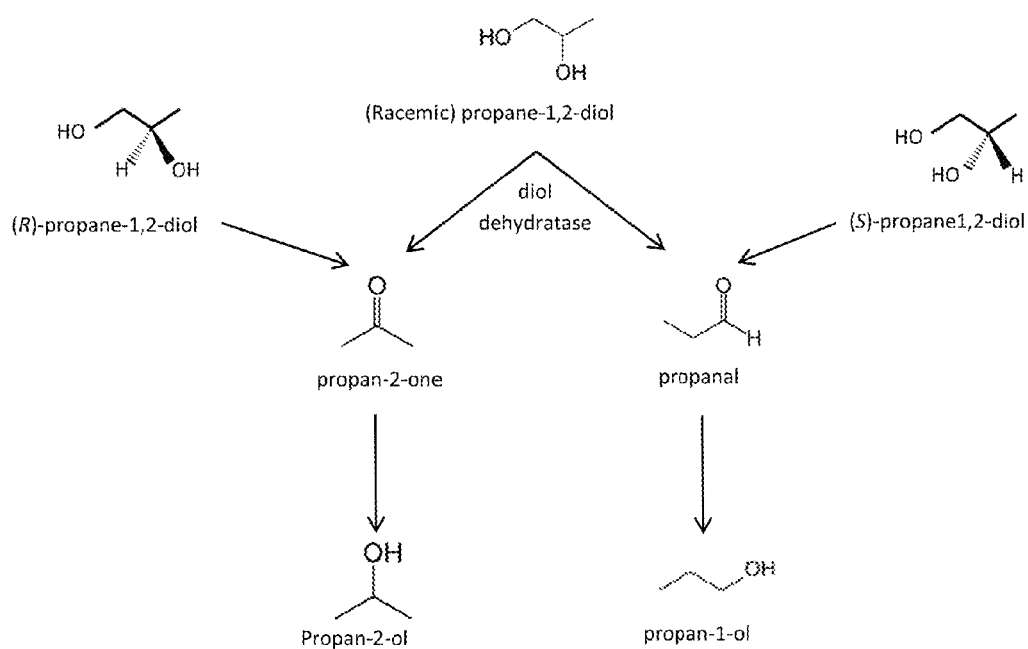
FIG. 1: Reaction pathway showing the stereospecific production of propanal, propan-2-one, propan-1-ol and/or propan-2-ol from propane-1,2-diol.

All known biosynthesis routes of propan-2-one and propan-2-ol start from acetyl-CoA via the intermediates acetoacetyl-CoA and acetoacetate. Here we present an alternative route from glyceraldehyde-3-phosphate or pyruvate via lactaldehyde and propane-1,2-diol (Berrios-Rivera, San, and Bennett 2003; Jain and Yan 2011) to propan-2-one and propan-2-ol. We describe here an enzyme that can stereospecifically convert propane-1,2-diol to propan-2-one and propanal. These products can then further be converted to propan-2-ol and propan-1-ol. Conversion of propane-1,2-diol to propanal has been described by another enzyme from Klebsiella pneumonia (Jain and Yan 2011), which however is unable to convert it to both propanal and also propan-2-one. Here we describe an enzyme and process for selective production of propan-2-one/propan-2-ol and/or propanal/propan-1-ol, either in an acetogenic cell that may contain this enzyme natively or in any native propane-1,2-diol producing host organism or in an engineered cell modified for propane-1,2-diol production as shown for E. coli or Saccharomyces cerevisiae (Berrios-Rivera, San, and Bennett 2003; Jain and Yan 2011). This reaction also allows for production of other commodities from precursors propan-2-one, propan-2-ol, propanal, propan-1-ol, for example isobutylene, that can be produced from propan-2-one (van Leeuwen et al. 2012) (WO2011032934). Another advantage of the invention using the novel diol dehydratases lies in the nature of the enzyme mechanism. Diol dehydratases catalyze irreversible reactions, thus allowing a kinetic control element for efficient production as products cannot be re-utilized, an important consideration when designing synthetic pathways (Bar-Even et al. 2012; Bond-Watts, Bellerose, and Chang 2011).

The following is a description of the present invention, including preferred embodiments thereof, given in general terms. The invention is further elucidated from the disclosure given under the heading "Examples" herein below, which provides experimental data supporting the invention, specific examples of various aspects of the invention, and means of performing the invention.

Definitions

As referred to herein, a "fermentation broth" is a culture medium comprising at least a nutrient media and bacterial cells.

As referred to herein, a "shuttle microorganism" is a microorganism in which a methyltransferase enzyme is expressed and is distinct from the destination microorganism.

As referred to herein, a "destination microorganism" is a microorganism in which the genes included on an expression construct/vector are expressed and is distinct from the shuttle microorganism.

The terms "increasing the efficiency," "increased efficiency" and the like, when used in relation to a fermentation process, include, but are not limited to, increasing one or more of the rate of growth of microorganisms catalysing the fermentation, the growth and/or product production rate at elevated product concentrations, the volume of desired product produced per volume of substrate consumed, the rate of production or level of production of the desired product, and the relative proportion of the desired product produced compared with other by-products of the fermentation.

The phrase "substrate comprising carbon monoxide" and like terms should be understood to include any substrate in which carbon monoxide is available to one or more strains of bacteria for growth and/or fermentation, for example.

The phrase "gaseous substrate comprising carbon monoxide" and like phrases and terms includes any gas which contains a level of carbon monoxide. In certain embodiments the substrate contains at least about 20% to about 100% CO by volume, from 20% to 70% CO by volume, from 30% to 60% CO by volume, and from 40% to 55% CO by volume. In particular embodiments, the substrate comprises about 25%, or about 30%, or about 35%, or about 40%, or about 45%, or about 50% CO, or about 55% CO, or about 60% CO by volume.

The phrase "isolated" and like terms refer to a member of a population that has been removed from other members of the population. Typically the population is a mixed population and the isolated member is either a singleton or a member of a homogeneous population. The term may be used to describe a microorganism, a protein, a nucleic acid, and the like.

The phrase "recombinant" and like terms refers to a nucleic acid, protein or microorganism which contains portions of different individuals, different species, or different genera that have been joined together. Typically this is done using techniques of recombinant DNA, such that a composite nucleic acid is formed. The composite nucleic acid can be used to make a composite protein, for example. It can be used to make a fusion protein. It can be used to transform a microbe which maintains and replicates the composite nucleic acid and optionally expresses a protein, optionally a composite protein.

The term "stereospecific" and like terms refer to enzymes that differentially recognize enantiomers, and catalyze different reactions with the enantiomers. Thus only one enantiomer may be reacted, or each enantiomer may yield a distinct product.

While it is not necessary for the substrate to contain any hydrogen, the presence of $H_2$ should not be detrimental to product formation in accordance with methods of the invention. In particular embodiments, the presence of hydrogen results in an improved overall efficiency of alcohol production. For example, in particular embodiments, the substrate may comprise an approx 2:1, or 1:1, or 1:2 ratio of $H_2$: CO. In one embodiment the substrate comprises about 30% or less $H_2$ by volume, 20% or less $H_2$ by volume, about 15% or less $H_2$ by volume or about 10% or less $H_2$ by volume. In other embodiments, the substrate stream comprises low concentrations of $H_2$, for example, less than 5%, or less than 4%, or less than 3%, or less than 2%, or less than 1%, or is substantially hydrogen free. The substrate may also contain some $CO_2$ for example, such as about 1% to about 80% $CO_2$ by volume, or 1% to about 30% $CO_2$ by volume. In one embodiment the substrate comprises less than or equal to about 20% $CO_2$ by volume. In particular embodiments the substrate comprises less than or equal to about 15% $CO_2$ by volume, less than or equal to about 10% $CO_2$ by volume, less than or equal to about 5% $CO_2$ by volume or substantially no $CO_2$.

In the description which follows, embodiments of the invention are described in terms of delivering and fermenting a "gaseous substrate containing CO." However, it should be appreciated that the gaseous substrate may be provided in alternative forms. For example, the gaseous substrate containing CO may be provided dissolved in a liquid. Essentially, a liquid is saturated with a carbon monoxide containing gas and then that liquid is added to the bioreactor. This may be achieved using standard methodology. By way of example, a microbubble dispersion generator (Hensirisak et. al. Scale-up of microbubble dispersion generator for aerobic fermentation; Applied Biochemistry and Biotechnology Volume 101, Number 3/October, 2002) could be used. By way of further example, the gaseous substrate containing CO may be adsorbed onto a solid support. Such alternative methods are encompassed by use of the term "substrate containing CO" and the like.

In particular embodiments of the invention, the CO-containing gaseous substrate is an industrial off or waste gas. "Industrial waste or off gases" should be taken broadly to include any gases comprising CO produced by an industrial process and include gases produced as a result of ferrous metal products manufacturing, non-ferrous products manufacturing, petroleum refining processes, gasification of coal, gasification of biomass, electric power production, carbon black production, and coke manufacturing. Further examples may be provided elsewhere herein.

Unless the context requires otherwise, the phrases "fermenting," "fermentation process" or "fermentation reaction" and the like, as used herein, are intended to encompass both the growth phase and product biosynthesis phase of the process. As will be described further herein, in some embodiments the bioreactor may comprise a first growth reactor and a second fermentation reactor. As such, the addition of metals or compositions to a fermentation reaction should be understood to include addition to either or both of these reactors.

The term "bioreactor" includes a fermentation device consisting of one or more vessels and/or towers or piping arrangement, which includes the Continuous Stirred Tank Reactor (CSTR), Immobilized Cell Reactor (ICR), Trickle Bed Reactor (TBR), Bubble Column, Gas Lift Fermenter, Static Mixer, or other vessel or other device suitable for gas-liquid contact. In some embodiments the bioreactor may comprise a first growth reactor and a second fermentation reactor. As such, when referring to the addition of substrate to the bioreactor or fermentation reaction it should be understood to include addition to either or both of these reactors where appropriate.

"Exogenous nucleic acids" are nucleic acids which originate outside of the microorganism to which they are introduced. Exogenous nucleic acids may be derived from any appropriate source, including, but not limited to, the microorganism to which they are to be introduced (for example in a parental microorganism from which the recombinant microorganism is derived), strains or species of microorganisms which differ from the organism to which they are to be introduced, or they may be artificially or recombinantly created. If the nucleic acids are from a different species of microorganism and have a different sequence, they are heterologous. In one embodiment, the exogenous nucleic acids represent nucleic acid sequences naturally present within the microorganism to which they are to be introduced, and they are introduced to increase expression of or over-express a particular gene (for example, by increasing the copy number of the sequence (for example a gene), or introducing a strong or constitutive promoter to increase expression). In another embodiment, the exogenous nucleic acids represent nucleic acid sequences not naturally present within the microorganism to which they are to be introduced and allow for the expression of a product not naturally present within the microorganism or increased expression of a gene native to the microorganism (for example in the case of introduction of a regulatory element such as a promoter). The exogenous nucleic acid may be adapted to integrate into the genome of the microorganism to which it is to be introduced or to remain in an extra-chromosomal state.

"Exogenous" may also be used to refer to proteins. This refers to a protein that is not present in the parental microorganism from which the recombinant microorganism is derived.

The term "endogenous" as used herein in relation to a recombinant microorganism and a nucleic acid or protein refers to any nucleic acid or protein that is present in a parental microorganism from which the recombinant microorganism is derived.

Unless otherwise specified, "propane-1,2-diol" as referred to herein refers to a racemic mixture of the two enantiomers (R)-propane-1,2-diol and (S)-propane-1,2-diol. Unless otherwise specified, "propanol" as referred to herein refers to a mixture of the two isomers propan-1-ol and propan-2-ol. Where products of the reactions referred to herein comprise propan-1-ol or propan-2-ol, it will be understood by one of skill in the art that the corresponding intermediates propanal and propan-2-one may be additionally or alternatively produced. Isolation of the intermediate aldehyde or ketone compounds as a stand-alone product may be desirable in some situations and, where appropriate, such aldehyde and ketone products are intended to be included within the scope of the invention.

It should be appreciated that the invention may be practised using nucleic acids whose sequence varies from the sequences specifically exemplified herein provided they perform substantially the same function. For nucleic acid sequences that encode a protein or peptide this means that the encoded protein or peptide has substantially the same function. For nucleic acid sequences that represent promoter sequences, the variant sequence will have the ability to promote expression of one or more genes. Such nucleic acids may be referred to herein as "functionally equivalent variants." By way of example, functionally equivalent variants of a nucleic acid include allelic variants, fragments of a gene, genes which include mutations (deletion, insertion, nucleotide substitutions and the like) and/or polymorphisms and the like. Homologous genes from other microorganisms may also be considered as examples of functionally equivalent variants of the sequences specifically exemplified herein. These include homologous genes in species such as *Clostridium autoethanogenum, C. ljungdahlii, C. novyi* details of which are publicly available on websites such as Genbank or NCBI. The phrase "functionally equivalent variants" should also be taken to include nucleic acids whose sequence varies as a result of codon optimisation for a particular organism. "Functionally equivalent variants" of a nucleic acid herein will preferably have at least approximately 70%, preferably approximately 80%, more preferably approximately 85%, preferably approximately 90%, preferably approximately 95% or greater nucleic acid sequence identity with the nucleic acid identified.

It should also be appreciated that the invention may be practised using polypeptides whose sequence varies from the amino acid sequences specifically exemplified herein. These variants may be referred to herein as "functionally equivalent variants." A functionally equivalent variant of a protein or a peptide includes those proteins or peptides that share at least 40%, preferably 50%, preferably 60%, preferably 70%, preferably 75%, preferably 80%, preferably 85%, preferably 90%, preferably 95% or greater amino acid identity with the protein or peptide identified and has substantially the same function as the peptide or protein of interest. Such variants include within their scope fragments of a protein or peptide wherein the fragment comprises a truncated form of the polypeptide wherein deletions may be from 1 to 5, to 10, to 15, to 20, to 25 amino acids, and may extend from residue 1 through 25 at either terminus of the polypeptide, and wherein deletions may be of any length within the region; or may be at an internal location or a specific domain of the protein conferring a specific catalytic function and activity, or binding of substrate or co-factors. Functionally equivalent variants of the specific polypeptides herein should also be taken to include polypeptides expressed by homologous genes in other species of bacteria, for example as exemplified in the previous paragraph.

"Substantially the same function" as used herein is intended to mean that the nucleic acid or polypeptide is able to perform the function of the nucleic acid or polypeptide of which it is a variant. For example, a variant of an enzyme of the invention will be able to catalyse the same reaction as that enzyme. However, it should not be taken to mean that the variant has the same level of activity as the polypeptide or nucleic acid of which it is a variant.

One may assess whether a functionally equivalent variant has substantially the same function as the nucleic acid or polypeptide of which it is a variant using methods known to one of skill in the art. However, by way of example, assays to test for diol dehydratase activity are described in example sections and can be assessed using HPLC methods or by derivatising with 2,4-dinitrophenylhydrazine (Toraya et al. 1977).

"Over-express," "over expression" and like terms and phrases when used in relation to the invention should be taken broadly to include any increase in expression of one or more proteins (including expression of one or more nucleic acids encoding same) as compared to the expression level of the protein (including nucleic acids) of a parental microorganism under the same conditions. It should not be taken to mean that the protein (or nucleic acid) is expressed at any particular level.

"Attenuated expression" as referred to herein refers to the expression of a nucleic acid or protein that is decreased relative to the expression in a parental microorganism. Attenuated expression also includes "zero" expression which refers to the nucleic acid or protein not being expressed at all. The "zero" expression may be achieved by any method known to one of skill in the art including RNA silencing, modification of the expression process (for example, disruption of the promoter function), or complete or partial removal (i.e., "knock out") of the nucleic acid encoding the enzyme from the genome.

A "parental microorganism" is a microorganism from which a microorganism of the invention is derived. The microorganism of the invention may be derived by any method such as artificial or natural selection, mutation, or genetic recombination. The parental microorganism may be one that occurs in nature (i.e., a wild-type microorganism) or one that has been previously modified but which does not express or over-express one or more of the enzymes the subject of the present invention. Accordingly, the recombinant microorganisms of the invention may have been modified to express or over-express one or more enzymes that were not expressed or over-expressed in the parental microorganism.

The terms nucleic acid "constructs" or "vectors" and like terms should be taken broadly to include any nucleic acid (including DNA and RNA) suitable for use as a vehicle to transfer genetic material into a cell. The terms should be taken to include plasmids, viruses (including bacteriophage), cosmids and artificial chromosomes. Constructs or vectors may include one or more regulatory elements, an origin of replication, a multicloning site and/or a selectable marker. In one particular embodiment, the constructs or vectors are adapted to allow expression of one or more genes encoded by the construct or vector. Nucleic acid constructs or vectors include naked nucleic acids as well as nucleic acids formulated with one or more agents to facilitate delivery to a cell (for example, liposome-conjugated nucleic acid, an organism in which the nucleic acid is contained).

Disclosure

The inventors have found that propanal, propan-2-one, propan-1-ol and/or propan-2-ol can be produced by a carboxydotrophic microorganism when in the presence of a substrate comprising CO and propane-1,2-diol. The production of propan-2-one and/or propan- and/or propan-2-ol from a racemic mixture of propane-1,2-diol has never been shown before by a microorganism. Following further experimentation, the inventors have shown that fermentation of a substrate comprising (R)-propane-1,2-diol preferentially produces propan-2-one and/or propan-2-ol and a substrate comprising (S)-propane-1,2-diol preferentially produces propanal and/or propan-1-ol. The inventors believe that the reaction proceeds as shown in FIG. 1 in the carboxydotrophic microorganism catalyses the stereospecific dehydration of propane-1,2-diol to form either propanal (from the (S) enantiomer) or propan-2-one (from the (R) enantiomer). A diol dehydratase catalysing this reaction has been identified and isolated. The inventors believe that these compounds are then converted to the corresponding alcohol propan-1-ol or propan-2-ol by the action of an endogenous alcohol dehydrogenase(s). A secondary alcohol dehydrogenase has been identified and demonstrated to convert propan-2-one into propan-2-ol. Identified enzymes can be used for formation of propanal, propan-2-one, propan-1-ol and/or propan-2-ol in any recombinant organism that produces propane-1,2-diol as product or intermediate or has been engineered to do so (Jain and Yan 2011). This reaction also allows for production of other commodities as for example isobutylene that may be produced from precursors propan-2-one, propan-2-ol, propanal, propan-1-ol (van Leeuwen et al. 2012).

The invention provides a method for the production of propanal, propan-2-one, propan-1-ol and/or propan-2-ol, and optionally one or more other products, by microbial fermentation comprising fermenting a substrate comprising CO and propane-1,2-diol using a carboxydotrophic microorganism as defined herein. The methods of the invention may be used to reduce the total atmospheric carbon emissions from an industrial process.

The present invention may have advantages over producing biofuels such as propanol from sugar based substrates and provides an alternative means for the production of propanal, propan-2-one, propan-1-ol and propan-2-ol utilising waste gases including carbon monoxide from industrial processes.

The propane-1,2-diol may be added to the fermentation substrate by any method known to one of skill in the art. By way of example, the propane-1,2-diol may be added to the substrate prior to, concurrently with, or subsequently to the introduction of the microorganism to the substrate. Further, the CO and/or other components of the fermentation broth may be added to the substrate prior to, concurrently with, or subsequently to the introduction of the propane-1,2-diol.

The propane-1,2-diol present in the substrate may be produced by the carboxydotrophic microorganism that produces the propanal, propan-2-one, propan-1-ol and/or propan-2-ol and production of the propane-1,2-diol may be in the same bioreactor or a different bioreactor. In a further embodiment, the propane-1,2-diol is produced by a different microorganism in the same bioreactor or in a different bioreactor.

In particular embodiments, the microorganism also produces one or more other products for example ethanol, butanol and/or butanediol. It can be seen in FIG. 2 that ethanol co-production is observed in addition to the production of propanal, propan-2-one, propan-1-ol and/or propan-2-ol.

Preferably, the fermentation comprises the steps of anaerobically fermenting a substrate in a bioreactor to produce at least propanal, propan-2-one, propan-1-ol and/or propan-2-ol using a recombinant microorganism of the invention as defined herein.

Recombinant Microorganisms

The inventors have engineered recombinant organisms and methods of use thereof for the production of propanal, propan-2-one, propan-1-ol and/or propan-2-ol. The recombinant carboxydotrophic microorganisms express an exogenous diol dehydratase enzyme and are able to achieve a higher yield of propanal, propan-2-one, propan-1-ol and/or propan-2-ol from propane-1,2-diol than would be produced by a parental microorganism. Ratios of produced propanal, propan-2-one, propan-1-ol and/or propan-2-ol from propane-1,2-diol may also be modulated this way. The microorganism also produces propanal, propan-2-one, propan-1-ol and/or propan-2-ol at a faster rate than would be produced by a parental microorganism.

As can be seen from FIG. 1, the diol dehydratase enzyme catalyses the reaction of (R) and/or (S) propane-1,2-diol to the corresponding ketone/aldehyde, i.e., to propan-2-one or to propanal, respectively. While reference may be made in this specification to propanol being produced from propane-1,2-diol, it will be understood by one of skill in the art that such production is likely to be via the corresponding aldehyde/ketone intermediate. Through further research, the inventors have demonstrated that these aldehydes are reduced to the corresponding alcohol by one or more endogenous alcohol dehydrogenase enzymes expressed by the microorganism. It is envisaged that the one or more alcohol dehydrogenase enzymes may be overexpressed to increase the rate of reaction and/or the reaction yield of the propanol product. Alternatively, the expression of the one or more alcohol dehydrogenases may be attenuated so as to reduce the production of the alcohol and increase the production of the corresponding aldehyde.

The enzymes and functional variants of use in the microorganisms of the invention may be derived from any appropriate source, including different genera and species of bacteria, or other organisms. However, in one embodiment, the diol dehydratase is that derived from *Klebsiella pneumoniae* or *K. oxytoca* (EC 4.1.2.30), or a functionally equivalent variant thereof. In one embodiment the diol dehydratase enzyme (three subunits) is as defined in YP_002236780, YP_002236781, YP_002236782, or a functionally equivalent variant thereof. In a particular embodiment, the diol dehydratase is encoded by the diol dehydratase genes GI:206575748, GI:206575749, GI:206575750 of (*Klebsiella pneumonia*) and GI:868006, GI:868007, GI:868008 (*Klebsiella oxytoca*).

The inventors have identified a diol dehydratase enzyme (SEQ ID NO: 3) that has not previously been described in a carboxydotrophic microorganism. In one embodiment, the invention provides a carboxydotrophic microorganism adapted to over-express one or more diol dehydratase enzymes (for example SEQ ID NO: 3 or a functionally equivalent variant thereof) which are present in a parental microorganism. In one particular embodiment, the endogenous diol dehydratase enzyme is encoded by a nucleic acid as defined in SEQ ID NO: 4, or a functionally equivalent variant thereof.

In one embodiment, the recombinant organism comprises an enzyme that exhibits attenuated expression or is knocked out. In a particular embodiment, the enzyme is an alcohol dehydrogenase enzyme and the recombinant organism produces propanal and/or propan-2-one in addition to, or instead of propan-1-ol and/or propan-2-ol. In particular embodiments, the alcohol dehydrogenase enzyme is defined in SEQ ID NO: 5, or is a functionally equivalent variant thereof. In further embodiments, the alcohol dehydrogenase enzyme is encoded by a nucleic acid as defined in SEQ ID NO: 6.

In one embodiment, the microorganism comprises one or more exogenous nucleic acids adapted to increase expression of one or more endogenous nucleic acids and which one or more endogenous nucleic acids encode a diol dehydratase referred to hereinbefore.

In one embodiment, the microorganism is further adapted to express one or more exogenous enzymes involved in the biosynthesis of propane-1,2-diol including but not limited to methylglyoxal synthase (mgsA); methylglyoxal reductase (ydjG); secondary alcohol dehydrogenase (gldA/budC); lactaldehyde reductase/primary alcohol dehydrogenase (fucO). In a further aspect, the microorganism is adapted to overexpress one or more endogenous enzymes in the propane-1,2-diol biosynthesis pathway.

While the inventors have demonstrated the efficacy of the invention in *Clostridium autoethanogenum*, they contemplate that the invention is applicable to the wider group of carboxydotrophic acteogenic microorganisms as discussed further herein.

The microorganism may be adapted to express or over-express the one or more enzymes by any number of recombinant methods including, for example, increasing expression of endogenous genes (for example, by introducing a stronger or constitutive promoter to drive expression of a gene), increasing the copy number of a gene encoding a particular enzyme by introducing exogenous nucleic acids encoding and adapted to express the enzyme, or introducing an exogenous nucleic acid encoding and adapted to express an enzyme not naturally present within the parental microorganism.

In one embodiment, the microorganism comprises one or more exogenous nucleic acids adapted to increase expression of one or more nucleic acids native to the parental microorganism and which one or more nucleic acids encode one or more of the enzymes referred to herein before. In one embodiment, the one or more exogenous nucleic acid adapted to increase expression is a regulatory element. In one embodiment, the regulatory element is a promoter. In one embodiment, the promoter is a constitutive promoter that is preferably highly active under appropriate fermentation conditions. Inducible promoters could also be used. In preferred embodiments, the promoter is selected from the group comprising Wood-Ljungdahl gene cluster, a pyruvate:ferredoxin oxidoreductase promoter, an Rnf complex operon promoter, ATP synthase operon promoter or Phosphotransacetylase/Acetate kinase operon promoters. It will be appreciated by those of skill in the art that other promoters which can direct expression, preferably a high level of expression under appropriate fermentation conditions, would be effective as alternatives to the exemplified embodiments.

The microorganism may comprise one or more exogenous nucleic acids. Where it is desirable to transform the parental microorganism with two or more genetic elements (such as genes or regulatory elements (for example a promoter)) they may be contained on one or more exogenous nucleic acids.

In one embodiment, the one or more exogenous nucleic acids expressed or over-expressed by the microorganism is a nucleic acid construct or vector, in one particular embodiment a plasmid, encoding one or more of the enzymes referred to hereinbefore in any combination.

The nucleic acids of the invention may remain extra-chromosomal upon transformation of the parental microorganism or may intergrate into the genome of the parental microorganism. Accordingly, they may include additional nucleotide sequences adapted to assist integration (for example, a region which allows for homologous recombination and targeted integration into the host genome) or expression and replication of an extrachromosomal construct (for example, origin of replication, promoter and other regulatory elements or sequences).

In one embodiment, the exogenous nucleic acids encoding one or more enzymes as mentioned herein before will further comprise a promoter adapted to promote expression of the one or more enzymes encoded by the exogenous nucleic acids. In one embodiment, the promoter is a constitutive promoter that is preferably highly active under appropriate fermentation conditions. Inducible promoters could also be used. In preferred embodiments, the promoter is selected from the group comprising Wood-Ljungdahl gene cluster, a pyruvate:ferredoxin oxidoreductase promoter, an Rnf complex operon promoter, ATP synthase operon promoter and Phosphotransacetylase/Acetate kinase promoters. It will be appreciated by those of skill in the art that other promoters which can direct expression, preferably a high level of expression under appropriate fermentation conditions, would be effective as alternatives to the exemplified embodiments.

In one embodiment, the exogenous nucleic acid is an expression plasmid.

In one particular embodiment, the parental microorganism is selected from the group of carboxydotrophic acetogenic bacteria comprising *Clostridium autoethanogenum, Clostridium ljungdahlii, Clostridium ragsdalei, Clostridium carboxidivorans, Clostridium drakei, Clostridium scatologenes, Clostridium aceticum, Clostridium formicoaceticum,*

*Clostridium magnum, Butyribacterium methylotrophicum, Acetobacterium woodii, Alkalibaculum bacchii, Blautia producta, Eubacterium limosum, Moorella thermoacetica, Moorella thermautotrophica, Sporomusa ovata, Sporomusa silvacetica, Sporomusa sphaeroides, Oxobacter pfennigii,* and *Thermoanaerobacter kiuvi.*

In one particular embodiment, the parental microorganism is selected from the cluster of ethanologenic, acetogenic *Clostridia* comprising the species *C. autoethanogenum, C. ljungdahlii,* and *C. ragsdalei* and related isolates. These include but are not limited to strains *C. autoethanogenum* JAI-1$^T$ (DSM10061) (Abrini, Naveau, and Nyns 1994), *C. autoethanogenum* LBS1560 (DSM19630) (WO/2009/064200), *C. autoethanogenum* LBS1561 (DSM23693), *C. ljungdahlii* PETC$^T$ (DSM13528=ATCC 55383) (Tanner, Miller, and Yang 1993), *C. ljungdahlii* ERI-2 (ATCC 55380) (U.S. Pat. No. 5,593,886), *C. ljungdahlii* C-01 (ATCC 55988) (U.S. Pat. No. 6,368,819), *C. ljungdahlii* O-52 (ATCC 55989) (U.S. Pat. No. 6,368,819), *C. ragsdalei* P11$^T$ (ATCC BAA-622) (WO 2008/028055), related isolates such as "*C. coskatii*" (US20110229947) and "*Clostridium* sp." (Tyurin and Kiriukhin 2012), or mutated strains such as *C. ljungdahlii* OTA-1 (Tirado-Acevedo O. Production of Bioethanol from Synthesis Gas Using *Clostridium ljungdahlii*. PhD thesis, North Carolina State University, 2010). These strains form a subcluster within the Clostridial rRNA cluster I, and their 16S rRNA gene is more than 99% identical with a similar low GC content of around 30%. However, DNA-DNA reassociation and DNA fingerprinting experiments showed that these strains belong to distinct species (WO 2008/028055).

All species of this cluster have a similar morphology and size (logarithmic growing cells are between 0.5-0.7×3-5 µm), are mesophilic (optimal growth temperature between 30-37° C.) and strictly anaerobe (Abrini, Naveau, and Nyns 1994; Tanner, Miller, and Yang 1993)(WO 2008/028055). Moreover, they all share the same major phylogenetic traits, such as same pH range (pH 4-7.5, with an optimal initial pH of 5.5-6), strong autotrophic growth on CO containing gases with similar growth rates, and a similar metabolic profile with ethanol and acetic acid as main fermentation end product, and small amounts of 2,3-butanediol and lactic acid formed under certain conditions (Abrini, Naveau, and Nyns 1994; Köpke et al. 2011; Tanner, Miller, and Yang 1993)(WO 2008/028055). Indole production was observed with all three species as well. However, the species differentiate in substrate utilization of various sugars (e.g. rhamnose, arabinose), acids (e.g. gluconate, citrate), amino acids (e.g. arginine, histidine), or other substrates (e.g. betaine, butanol). Moreover some of the species were found to be auxotroph to certain vitamins (e.g. thiamine, biotin) while others were not. The organization and number of Wood-Ljungdahl pathway genes, responsible for gas uptake, has been found to be the same in all species, despite differences in nucleic and amino acid sequences (Köpke et al. 2011).

In one embodiment, the parental strain uses CO as its sole carbon and energy source.

In one embodiment the parental microorganism is *Clostridium autoethanogenum* or *Clostridium ljungdahlii*. In one particular embodiment, the microorganism is *Clostridium autoethanogenum* DSM23693 a derivate of strain DSM10061. *C. autoethanogenum*. In another particular embodiment, the microorganism is *Clostridium ljungdahlii* DSM13528 (or ATCC55383).

Nucleic Acids
Isolated Nucleic Acid (Identified from *C. Autoethanogenum* and *C. Ljungdahlii*)

The inventors have identified a nucleic acid encoding a diol dehydratase in two carboxydotrophic acetogens *C. autoethanogenum* and *C. ljungdahlii*. The nucleic acid encodes a diol dehydratase which catalyses the conversion of propane-1,2-diol to propanal, propan-2-one, propan-1-ol and/or propan-2-ol.

In one embodiment the nucleic acid encoding a diol dehydratase is defined in SEQ ID NO: 1-2 (*C. autoethanogenum*) and CLJU_c11830; 9444800 and CLJU_c11831; 9444801 (*C. ljungdahlii*) or is a functionally equivalent variant thereof.

In one embodiment, the nucleic acids of the invention further comprise a promoter. In one embodiment, the promoter allows for constitutive expression of the genes under its control. Persons of skill in the art will readily appreciate promoters of use in the invention. Preferably, the promoter can direct a high level of expression under appropriate fermentation conditions. In a particular embodiment a Wood-Ljungdahl cluster promoter is used. In other particular embodiments a pyruvate:ferredoxin oxidoreductase promoter, an Rnf complex operon promoter, ATP synthase operon promoter or a Phosphotransacetylase/Acetate kinase operon promoter is used. In one particular embodiment, the promoter is from *C. autoethanogenum*.

The invention also provides one or more nucleic acids or nucleic acid constructs comprising one or more nucleic acids of the invention of use in generating a recombinant microorganism of the invention.

In one embodiment, the nucleic acid comprises sequences encoding one or more of the enzymes of the invention defined herein before which when expressed in a microorganism allows the microorganism to produce propanal, propan-2-one, propan-1-ol and/or propan-2-ol by fermentation of a substrate comprising CO. In one particular embodiment, the invention provides a nucleic acid encoding two enzymes which when expressed in a microorganism allows the microorganism to produce propanal, propan-2-one, propan-1-ol and/or propan-2-ol by fermentation of a substrate comprising CO. In a particular embodiment, the two enzymes are diol dehydratase and an alcohol dehydrogenase as defined herein.

Exemplary amino acid sequences and nucleic acid sequences encoding enzymes described herein are provided herein or can be obtained from GenBank as mentioned hereinbefore. However, skilled persons will readily appreciate alternative nucleic acids sequences encoding the enzymes or functionally equivalent variants thereof, having regard to the information contained herein, in GenBank and other databases, and the genetic code.

The invention also provides propanal, propan-2-one, propan-1-ol and/or propan-2-ol when produced by the method of the first aspect.

In one embodiment, the nucleic acid is a nucleic acid construct or vector. In one particular embodiment, the nucleic acid construct or vector is an expression construct or vector, however other constructs and vectors, such as those used for cloning are encompassed by the invention. In one particular embodiment, the expression construct or vector is a plasmid.

It will be appreciated that an expression construct/vector of the present invention may contain any number of regulatory elements in addition to the promoter as well as additional genes suitable for expression of further proteins if desired. In one embodiment the expression construct/vector includes one promoter. In another embodiment, the expression construct/vector includes two or more promoters. In one particular embodiment, the expression construct/vector includes one promoter for each gene to be expressed. In one embodiment, the expression construct/vector includes one or more ribosomal binding sites, preferably a ribosomal binding site for each gene to be expressed.

It will be appreciated by those of skill in the art that the nucleic acid sequences and construct/vector sequences described herein may contain standard linker nucleotides such as those required for ribosome binding sites and/or restriction sites. Such linker sequences should not be interpreted as being required and do not provide a limitation on the sequences defined.

Nucleic acids and nucleic acid constructs, including expression constructs/vectors of the invention may be constructed using any number of techniques standard in the art. For example, chemical synthesis or recombinant techniques may be used. Such techniques are described, for example, in Sambrook et al (Molecular Cloning: A laboratory manual, Cold Spring Harbor Laboratory Press, Cold Spring Harbor, N.Y., 1989). Further exemplary techniques are described in the Examples section herein after. Essentially, the individual genes and regulatory elements will be operably linked to one another such that the genes can be expressed to form the desired proteins. Suitable vectors for use in the invention will be appreciated by those of ordinary skill in the art. However, by way of example, the following vectors may be suitable: pMTL80000 vectors, pIMP1, pJIR750, and the plasmids exemplified in the Examples section herein after.

It should be appreciated that nucleic acids of the invention may be in any appropriate form, including RNA, DNA, or cDNA.

The invention also provides host organisms, particularly microorganisms, and including viruses, bacteria, and yeast, comprising any one or more of the nucleic acids described herein.

Method of Producing Microorganisms

The one or more exogenous nucleic acids may be delivered to a parental microorganism as naked nucleic acids or may be formulated with one or more agents to facilitate the transformation process (for example, liposome-conjugated nucleic acid, an organism in which the nucleic acid is contained). The one or more nucleic acids may be DNA, RNA, or combinations thereof, as is appropriate. Restriction inhibitors may be used in certain embodiments; see, for example Murray, N. E. et al. (2000) *Microbial. Molec. Biol. Rev.* 64, 412.)

The microorganisms of the invention may be prepared from a parental microorganism and one or more exogenous nucleic acids using any number of techniques known in the art for producing recombinant microorganisms. By way of example only, transformation (including transduction or transfection) may be achieved by electroporation, ultrasonication, polyethylene glycol-mediated transformation, chemical or natural competence, protoplast transformation, prophage induction or conjugation. Suitable transformation techniques are described for example in, Sambrook J, Fritsch E F, Maniatis T: Molecular Cloning: A laboratory Manual, Cold Spring Harbour Laboratory Press, Cold Spring Harbour, 1989.

Electroporation has been described for several carboxydotrophic acetogens as *C. ljungdahlii* (Köpke et al. 2010) (PCT/NZ2011/000203; WO2012/053905), *C. autoethanogenum* (PCT/NZ2011/000203; WO2012/053905), *C. aceticum* (Schiel-Bengelsdorf and Peter Dürre 2012) or *Acetobacterium woodii* (Strätz et al. 1994) and is a standard method used in many *Clostridia* such as *C. acetobutylicum* (Mermelstein et al., 1992, *Biotechnology*, 10, 190-195), *C. cellulolyticum* (Jennert et al., 2000, *Microbiology*, 146: 3071-3080) or *C. thermocellum* (Tyurin et al., 2004, *Appl. Environ. Microbiol.* 70: 883-890). Prophage induction has been demonstrated for carboxydotrophic acetogen as well in case of *C. scatologenes* (Prasanna Tamarapu Parthasarathy, 2010, Development of a Genetic Modification System in *Clostridium scatologenes* ATCC 25775 for Generation of Mutants, Masters Project Western Kentucky University), while conjugation has been described as method of choice for many *Clostridia* including *Clostridium difficile* (Herbert et al., 2003, *FEMS Microbiol. Lett.* 229: 103-110) or *C. acetobuylicum* (Williams et al., 1990, *J. Gen. Microbiol.* 136: 819-826) and could be used in a similar fashion for carboxydotrophic acetogens.

In certain embodiments, due to the restriction systems which are active in the microorganism to be transformed, it is necessary to methylate the nucleic acid to be introduced into the microorganism. This can be done using a variety of techniques, including those described below, and further exemplified in the Examples section herein after.

By way of example, in one embodiment, a recombinant microorganism of the invention is produced by a method comprises the following steps:

introduction into a shuttle microorganism of (i) of an expression construct/vector as described herein and (ii) a methylation construct/vector comprising a methyltransferase gene; expression of the methyltransferase gene; and isolation of one or more constructs/vectors from the shuttle microorganism; and, introduction of the one or more construct/vector into a destination microorganism.

In one embodiment, the methyltransferase gene of step B is expressed constitutively. In another embodiment, expression of the methyltransferase gene of step B is induced.

The shuttle microorganism is a microorganism, preferably a restriction negative microorganism, that facilitates the methylation of the nucleic acid sequences that make up the expression construct/vector. In a particular embodiment, the shuttle microorganism is a restriction negative *E. coli*, *Bacillus subtillis*, or *Lactococcus lactis*.

The methylation construct/vector comprises a nucleic acid sequence encoding a methyltransferase.

Once the expression construct/vector and the methylation construct/vector are introduced into the shuttle microorganism, the methyltransferase gene present on the methylation construct/vector is induced. Induction may be by any suitable promoter system although in one particular embodiment of the invention, the methylation construct/vector comprises an inducible lac promoter and is induced by addition of lactose or an analogue thereof, more preferably isopropyl-β-D-thiogalactoside (IPTG). Other suitable promoters include the ara, tet, or T7 system. In a further embodiment of the invention, the methylation construct/vector promoter is a constitutive promoter.

In a particular embodiment, the methylation construct/vector has an origin of replication specific to the identity of the shuttle microorganism so that any genes present on the methylation construct/vector are expressed in the shuttle microorganism. Preferably, the expression construct/vector has an origin of replication specific to the identity of the destination microorganism so that any genes present on the expression construct/vector are expressed in the destination microorganism.

Expression of the methyltransferase enzyme results in methylation of the genes present on the expression construct/vector. The expression construct/vector may then be isolated from the shuttle microorganism according to any one of a number of known methods. By way of example only, the methodology described in the Examples section described hereinafter may be used to isolate the expression construct/vector.

In one particular embodiment, both construct/vector are concurrently isolated.

The expression construct/vector may be introduced into the destination microorganism using any number of known methods. However, by way of example, the methodology described in the Examples section hereinafter may be used. Since the expression construct/vector is methylated, the nucleic acid sequences present on the expression construct/vector are able to be incorporated into the destination microorganism and successfully expressed.

It is envisaged that a methyltransferase gene may be introduced into a shuttle microorganism and over-expressed. Thus, in one embodiment, the resulting methyltransferase enzyme may be collected using known methods and used in vitro to methylate an expression plasmid. The expression construct/vector may then be introduced into the destination microorganism for expression. In another embodiment, the methyltransferase gene is introduced into the genome of the shuttle microorganism followed by introduction of the expression construct/vector into the shuttle microorganism, isolation of one or more constructs/vectors from the shuttle microorganism and then introduction of the expression construct/vector into the destination microorganism.

It is envisaged that the expression construct/vector and the methylation construct/vector as defined above may be combined to provide a composition of matter. Such a composition has particular utility in circumventing restriction barrier mechanisms to produce the recombinant microorganisms of the invention.

In one particular embodiment, the expression construct/vector and/or the methylation construct/vector are plasmids.

Persons of ordinary skill in the art will appreciate a number of suitable methyltransferases of use in producing the microorganisms of the invention. However, by way of example the *Bacillus subtilis* phage ΦT1 methyltransferase and the methyltransferase described in the Examples herein after may be used. In one embodiment, the methyltransferase has the amino acid sequence of SEQ ID NO: 7, or is a functionally equivalent variant thereof. Nucleic acids encoding suitable methyltransferases will be readily appreciated having regard to the sequence of the desired methyltransferase and the genetic code. In one embodiment, the nucleic acid encoding a methyltransferase is as described in the Examples herein after (for example the nucleic acid of SEQ ID NO: 8, or it is a functionally equivalent variant thereof).

Any number of constructs/vectors adapted to allow expression of a methyltransferase gene may be used to generate the methylation construct/vector. However, by way of example, the plasmid described in the Examples section hereinafter may be used.

Methods of Production

In an embodiment of the invention, the gaseous substrate fermented by the microorganism is a gaseous substrate containing CO. The gaseous substrate may be a CO-containing waste gas obtained as a by-product of an industrial process, or from some other source such as from automobile exhaust fumes. In certain embodiments, the industrial process is selected from the group consisting of ferrous metal products manufacturing, such as a steel mill, non-ferrous products manufacturing, petroleum refining processes, gasification of coal, electric power production, carbon black production, ammonia production, methanol production and coke manufacturing. In these embodiments, the CO-containing gas may be captured from the industrial process before it is emitted into the atmosphere, using any convenient method. The CO may be a component of syngas (gas comprising carbon monoxide and hydrogen). The CO produced from industrial processes is normally flared off to produce $CO_2$ and therefore the invention has particular utility in reducing $CO_2$ greenhouse gas emissions and producing a biofuel. Depending on the composition of the gaseous CO-containing substrate, it may also be desirable to treat it to remove any undesired impurities, such as dust particles before introducing it to the fermentation. For example, the gaseous substrate may be filtered or scrubbed using known methods.

It will be appreciated that for growth of the bacteria and the production of products to occur, in addition to the CO-containing substrate gas, a suitable liquid nutrient medium will need to be fed to the bioreactor.

In particular embodiments of the method aspects, the fermentation occurs in an aqueous culture medium. In particular embodiments of the method aspects, the fermentation of the substrate takes place in a bioreactor.

The substrate and media may be fed to the bioreactor in a continuous, batch or batch fed fashion. A nutrient medium will contain vitamins and minerals sufficient to permit growth of the micro-organism used. Anaerobic media suitable for fermentation using CO are known in the art. For example, suitable media are described Biebel (2001). In one embodiment of the invention the media is as described in the Examples section herein after.

The fermentation should desirably be carried out under appropriate fermentation conditions for the production of the biofuel to occur. Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO in the liquid phase does not become limiting, and maximum product concentrations to avoid product inhibition.

In addition, it is often desirable to increase the CO concentration of a substrate stream (or CO partial pressure in a gaseous substrate) and thus increase the efficiency of fermentation reactions where CO is a substrate. Operating at increased pressures allows a significant increase in the rate of CO transfer from the gas phase to the liquid phase where it can be taken up by the micro-organism as a carbon source for the production of fermentation. This in turn means that the retention time (defined as the liquid volume in the bioreactor divided by the input gas flow rate) can be reduced when bioreactors are maintained at elevated pressure rather than atmospheric pressure. The optimum reaction conditions will depend partly on the particular micro-organism of the invention used. However, in general, it is preferred that the fermentation be performed at pressure higher than ambient pressure. Also, since a given CO conversion rate is in part a function of the substrate retention time, and achieving a desired retention time in turn dictates the required volume of a bioreactor, the use of pressurized systems can greatly reduce the volume of the bioreactor required, and consequently the capital cost of the fermentation equipment. According to examples given in U.S. Pat. No. 5,593,886, reactor volume can be reduced in linear proportion to increases in reactor operating pressure, i.e. bioreactors operated at 10 atmospheres of pressure need only be one tenth the volume of those operated at 1 atmosphere of pressure.

By way of example, the benefits of conducting a gas-to-ethanol fermentation at elevated pressures have been described. For example, WO 02/08438 describes gas-to-ethanol fermentations performed under pressures of 30 psig and 75 psig, giving ethanol productivities of 150 g/l/day and 369 g/l/day respectively. However, example fermentations performed using similar media and input gas compositions at atmospheric pressure were found to produce between 10 and 20 times less ethanol per liter per day.

It is also desirable that the rate of introduction of the CO-containing gaseous substrate is such as to ensure that the concentration of CO in the liquid phase does not become limiting. This is because a consequence of CO-limited conditions may be that one or more product is consumed by the culture.

The composition of gas streams used to feed a fermentation reaction can have a significant impact on the efficiency and/or costs of that reaction. For example, O2 may reduce the efficiency of an anaerobic fermentation process. Processing of unwanted or unnecessary gases in stages of a fermentation process before or after fermentation can increase the burden on such stages (e.g. where the gas stream is compressed before entering a bioreactor, unnecessary energy may be used to compress gases that are not needed in the fermentation). Accordingly, it may be desirable to treat substrate streams, particularly substrate streams derived from industrial sources, to remove unwanted components and increase the concentration of desirable components.

In certain embodiments a culture of a bacterium of the invention is maintained in an aqueous culture medium. Preferably the aqueous culture medium is a minimal anaerobic microbial growth medium. Suitable media are known in the art and described for example in U.S. Pat. Nos. 5,173,429 and 5,593,886 and WO 02/08438, and as described in the Examples section herein after.

Propanal, propan-2-one, propan-1-ol and/or propan-2-ol, or a mixed stream containing Propanal, propan-2-one, propan-1-ol and/or propan-2-ol and/or one or more other products, may be recovered from the fermentation broth by methods known in the art, such as fractional distillation or evaporation, pervaporation, gas stripping and extractive fermentation, including for example, liquid-liquid extraction. Products may also diffuse or secrete into media, from which they can extracted by phase separation.

In certain preferred embodiments of the invention, propanal, propan-2-one, propan-1-ol and/or propan-2-ol and one or more products are recovered from the fermentation broth by continuously removing a portion of the broth from the bioreactor, separating microbial cells from the broth (conveniently by filtration), and recovering one or more products from the broth. Alcohols may conveniently be recovered for example by distillation. Propan-2-one may be recovered for example by distillation. Any acids produced may be recovered for example by adsorption on activated charcoal. The separated microbial cells are preferably returned to the fermentation bioreactor. The cell free permeate remaining after any alcohol(s) and acid(s) have been removed is also preferably returned to the fermentation bioreactor. Additional nutrients (such as B vitamins) may be added to the cell free permeate to replenish the nutrient medium before it is returned to the bioreactor.

Also, if the pH of the broth was adjusted as described above to enhance adsorption of acetic acid to the activated charcoal, the pH should be re-adjusted to a similar pH to that of the broth in the fermentation bioreactor, before being returned to the bioreactor.

EXAMPLES

The invention will now be described in more detail with reference to the following non-limiting examples.

Microorganisms and Growth Conditions

*Clostridium autoethanogenum* DSM23693, *C. carboxidivorans* DSM15243, and *C. ljungdahlii* DSM13528, and *C. butyricum* DSM 10702 were sourced from DSMZ (The German Collection of Microorganisms and Cell Cultures, Inhoffenstraße 7 B, 38124 Braunschweig, Germany). *C. autoethanogenum* DSM23693 is a derivate of *C. autoethanogenum* DSM10061.

*E. coli* were cultivated under both aerobic and anaerobic conditions, while all other strains were grown strictly anaerobically in a volume of 50 ml liquid media in serum bottles with fructose (heterotrophic growth) or 30 psi CO-containing steel mill gas (collected from New Zealand Steel site in Glenbrook, NZ; composition: 44% CO, 32% $N_2$, 22% $CO_2$, 2% $H_2$) in the headspace (autotrophic growth).

Media was prepared using standard anaerobic techniques (Hungate R E: A roll tube method for cultivation of strict anaerobes, in Norris J R and Ribbons D W (eds.), Methods in Microbiology, vol. 3B. Academic Press, New York, 1969: 117-132; Wolfe R S: Microbial formation of methane. *Adv Microb Physiol* 1971, 6: 107-146) according to formulations are given in Tab. 2-4. For solid media, 1.2% Bacto agar (BD, Frankton Lakes, N.J. 07417, USA) was added.

All strains were grown at 37° C.

PETC Medium (*C. Autoethanogenum, C. Ljungdahlii*, and *C. Ragsdalei* pH5.6, *C. Butyricum* pH6.8)

| Media component | Concentration per 1.0 L of media |
|---|---|
| $NH_4Cl$ | 1 g |
| KCl | 0.1 g |
| $MgSO_4 \cdot 7H_2O$ | 0.2 g |
| NaCl | 0.8 g |
| $KH_2PO_4$ | 0.1 g |
| $CaCl_2$ | 0.02 g |
| Trace metal solution (see below) | 10 ml |
| Wolfe's vitamin solution (see below) | 10 ml |
| Yeast Extract (optional) | 1 g |
| Resazurin (2 g/L stock) | 0.5 ml |
| $NaHCO_3$ | 2 g |
| Reducing agent | 0.006-0.008% (v/v) |
| Fructose (for heterotrophic growth) | 5 g |

| Trace metal solution | per L of stock |
|---|---|
| Nitrilotriacetic Acid | 2 g |
| $MnSO_4 \cdot H_2O$ | 1 g |
| $Fe(SO_4)_2(NH_4)_2 \cdot 6H_2O$ | 0.8 g |
| $CoCl_2 \cdot 6H_2O$ | 0.2 g |
| $ZnSO_4 \cdot 7H_2O$ | 0.2 mg |
| $CuCl_2 \cdot 2H_2O$ | 0.02 g |
| $NaMoO_4 \cdot 2H_2O$ | 0.02 g |
| $Na_2SeO_3$ | 0.02 g |
| $NiCl_2 \cdot 6H_2O$ | 0.02 g |
| $Na_2WO_4 \cdot 2H_2O$ | 0.02 g |

| Reducing agent stock | per 100 mL of stock |
|---|---|
| NaOH | 0.9 g |
| Cystein•HCl | 4 g |
| $Na_2S$ | 4 g |

Reinforced Clostridial Medium RCM (*C. Carboxidivorans*)

| Media component | Concentration per 1.0 L of media |
|---|---|
| Pancreatic Digest of Casein | 5 g |
| Proteose Peptone No. 3 | 5 g |
| Beef Extract | 10 g |
| Yeast Extract | 3 g |
| Dextrose | 5 g |
| NaCl | 5 g |
| Soluble starch | 1 g |
| Cystein•HCl | 0.5 g |
| Sodium Acetate | 3 g |
| Fructose | 5 g |

Luria Bertani Medium LB (*E. coli*)

| Media component | Concentration per 1.0 L of media |
|---|---|
| Tryptone | 10 g |
| Yeast Extract | 5 g |
| NaCl | 10 g |

When specified, propane-1,2-diol was added to a final concentration of 5 g L-1 at the time of inoculation and final metabolite analysis was conducted after cultures had grown for 40 hours.

Analysis of Metabolites

To remove proteins and other cell residues, 400 µl samples were mixed with 100 µl of a 2% (w/v) 5-Sulfosalicylic acid and centrifuged at 14,000×g for 3 min to separate precipitated residues. 10 µl of the supernatant were then injected into the HPLC for analyses. HPLC analysis of 2,3-butanediol, 2-butanol and other metabolites was performed using an Agilent 1100 Series HPLC system equipped with a RID operated at 35° C. (Refractive Index Detector) and an Aminex HPX-87H column (300×7.8 mm, particle size 9 µm) kept at 35° C. Slightly acidified water was used (0.005 M $H_2SO_4$) as mobile phase with a flow rate of 0.6 ml/min. For distinction of 2,3-butanediol sterioisomers HPLC analysis was performed using an Agilent 1100 Series HPLC system equipped with a RID operated at 35° C. (Refractive Index Detector) and an Alltech IOA-2000 Organic acid column (150×6.5 mm, particle size 8 µm) kept at 60° C. Slightly acidified water was used (0.005 M $H_2SO_4$) as mobile phase with a flow rate of 0.25 ml/min.

GC analysis of propan-2-one, propan-2-ol and other metabolites was performed using an Agilent 6890N headspace GC equipped with a Supelco PDMS 100 1 cm fiber, an Alltech EC-1000 (30 m×0.25 mm×0.25 µm) column, and a flame ionization detector (FID). 5 ml samples were transferred into a Hungate tube, heated to 40° C. in a water bath and exposed to the fiber for exactly 5 min. The injector was kept at 250° C. and helium with a constant flow of 1 ml/min was used as carrier gas. The oven program was 40° C. for 5 min, followed by an increase of 10° C./min up to 200° C. The temperature was then further increased to 220° C. with a rate of 50° C./min followed by a 5 min hold this temperature, before the temperature was decreased to 40° C. with a rate of 50° C./min and a final 1 min hold. The FID was kept at 250° C. with 40 ml/min hydrogen, 450 ml/min air and 15 ml/min nitrogen as make up gas.

Figure 2:
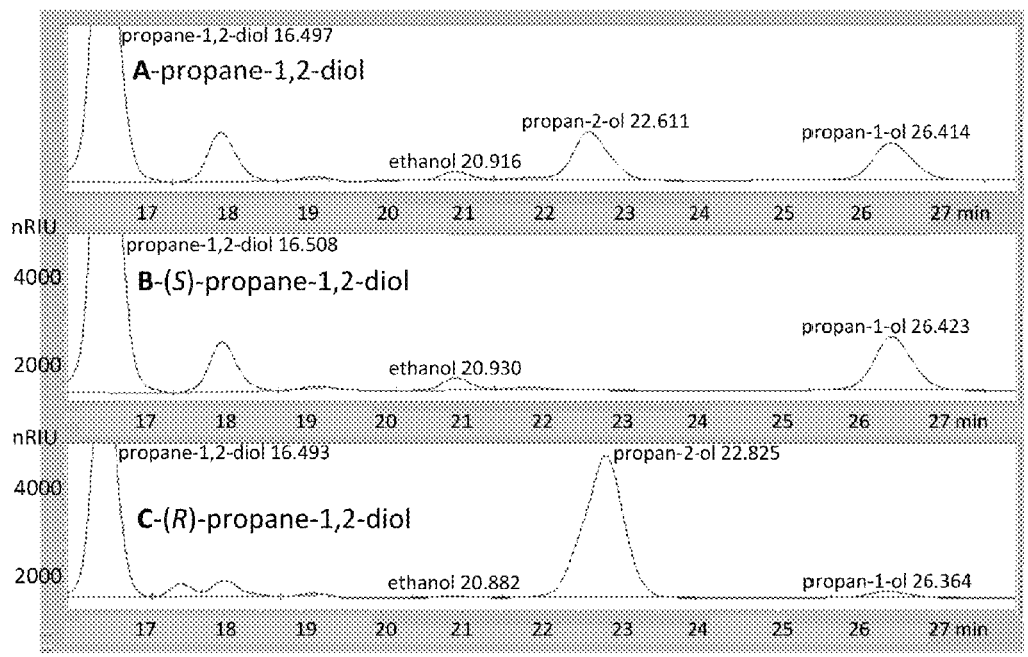
FIG. 2: HPLC chromatograms showing the production of products propanal, propan-1-ol, propan-2-ol and ethanol from A—propane-1,2-diol, B—(S)-propane-1,2-diol and C—(R)-propane-1,2-diol. Propan-2-one is a co-product in A and C but is obscured by the propan-2-ol peak. Further analysis has eluted propan-2-one separately using a different Gas chromatography method.
Figure 3:
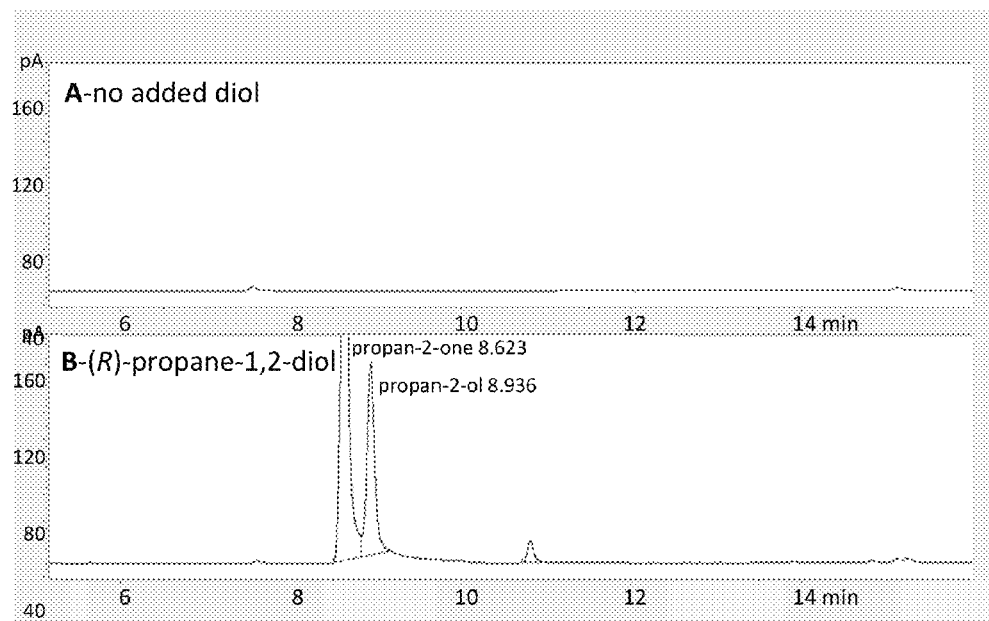
FIG. 3. Gas Chromatogram of headspace over cultures of C. autoethanogenum highlights retention time of propan-2-one and propan-2-ol. Culture with no propane-1,2diol added, A; and culture with (R)-propan-2-ol added, B.

Identification of Reaction of Propane-1,2-diol to Propan-2-one, Propan-2-ol, Propanal, Propan-1-ol Propane-1,2-diol (racemic) was added to cultures of *C. autoethanogenum* at the time of inoculation. After two days of growth the propane-1,2-diol was surprisingly found to be converted to propan-1-ol and propan-2-ol as seen in FIG. 2. When (S)-propane-1,2-diol is added to the culture it is converted to propan-1-ol, and the intermediate, propanal, can be seen (FIG. 2). When (R)-propane-1,2-diol is added to the culture it is converted to propan-2-ol (FIG. 2). The HPLC method used cannot resolve propan-2-ol and propan-2-one, but by GC the presence of the intermediate propan-2-one can be seen (FIG. 3).

Conversion of propane-1,2-diol to propanal has been described for several diol dehydratase enzymes. There are two types of previously described diol dehydratase enzymes, a B12-dependent (propane)diol dehydratase type (EC 4.2.1.28) as for example of *Klebsiella pneumonia* or *K. oxytoca* (Toraya T, Shirakashi T, Kosuga T 1976), and a B-12 independent glycerol/diol dehydratase type (EC 4.1.2.30) as for example from *Clostridium glycolicum* or *C. butyricum* (Brien et al. 2004; Hartmanis and Stadtman 1986) (Table 1).

TABLE 1

| B12 independent dehydratase (EC 4.2.1.28) | | |
|---|---|---|
| Organism | glycerol dehydratase | activator |
| *Clostridium glycolicum* | — | — |
| *Clostridium butyricum* | ABX65443 | ABX65444 |
| *Clostridium* sp. | AAY34226 | ACF15539 |
| *Clostridium diolis* | ACI39933 | ACI39932 |
| *Roseburia inulinivorans* | ZP_03753304 | ZP_03753303 |

| B12 dependent dehydratase (EC 4.1.2.30) | | |
|---|---|---|
| Organism | alpha | beta | Gamma |
| *Klebsiella oxytoca* | 1DIO_A | 1DIO_B | 1DIO_G |
| *Salmonella enterica* | NP_460985 | NP_460986 | NP_460987 |
| *Citobacter koseri* | YP_001452384 | YP_001452383 | YP_001452382 |
| *Klebsiella pneumoniae* | YP_002236782 | YP_002236781 | YP_002236780 |
| *Escherichia coli* | YP_001463342 | YP_001463343 | YP_001463344 |

However, conversion of propane-1,2-diol to propan-2-one and propan-2-ol has never been observed and an enzyme catalysing this reaction is previously unknown. Also no stereospecific conversion of propane-1,2-diol has been described. The inventors identified here a stereospecific reaction of propane-1,2-diol to propan-2-one plus propan-2-ol and/or propanal and propan-1-ol as depicted in FIG. 1. Without being bound to this theory, the inventors think, the novel diol dehydratase of *C. autoethanogenum* stereospecifically converts (R)-propane-1,2-diol to propan-2-one and (S)-propane-1,2-diol to propan-2-ol.

Propan-2-one conversion to propan-2-ol is then catalyzed by a primary:secondary alcohol dehydrogenase (SEQ ID NO: 5 and 6) as described in U.S. patent application Ser. No. 13/403,972 and U.S. Ser. No. 13/459,211 earlier. The primary function of such an enzyme can also catalyze the reduction of propanal to propan-1-ol (Ismaiel et al. 1993), as many other primary alcohol dehydrogenases and uspecific ethanol dehydrogenases.

Identification of a Diol Dehydratase Gene

A search in the genome of *C. autoethanogenum* identified a gene (SEQ ID NO:3 and 4) that has low homology (Identities=503/844 (59%), Positives=626/844 (74%), Gaps=63/844 (7%), respectively Identities=125/257 (49%), Positives=181/257 (70%), Gaps=0/257 (0%)) to the B12-independent glycerol dehydratase of *C. butyriucm* (ABX65443 and ABX65444) on amino acid level.

This enzyme has been knocked out in *C. autoethanogenum* using the ClosTron system (Heap et al. 2007), which resulted in a strain unable to utilize propane-1,2-diol and form any propan-2-one, propan-2-ol, propanal, or propan-1-ol, thus demonstrating that this enzyme represents the novel diol dehydratase responsible for stereospecific conversion of propane-1,2-diol into propan-2-one and propanal.

The Perutka algorithm hosted at ClosTron.com was used to identify the group II intron target site between bases 2052 and 2053 on the sense strand of the gene and to design the intron targeting region (SEQ ID NO:13) which was chemically synthesized in pMTL007C-E2 vector. The final vector, pMTL007C-E2-pfl-1136-2052!2053s, contains a Retro-tranposition-Activated ermB Marker (RAM) which confers resistance to antibiotic Clarithromycin upon insertion into the target site.

Figure 10:
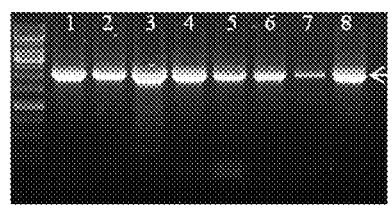
FIG. 10: PCR confirmation of group II intron insertion in diol dehydratase gene using primers Og84f and Og85r. 8 clones after Clarithromycin selection were randomly screened.
Figure 11:
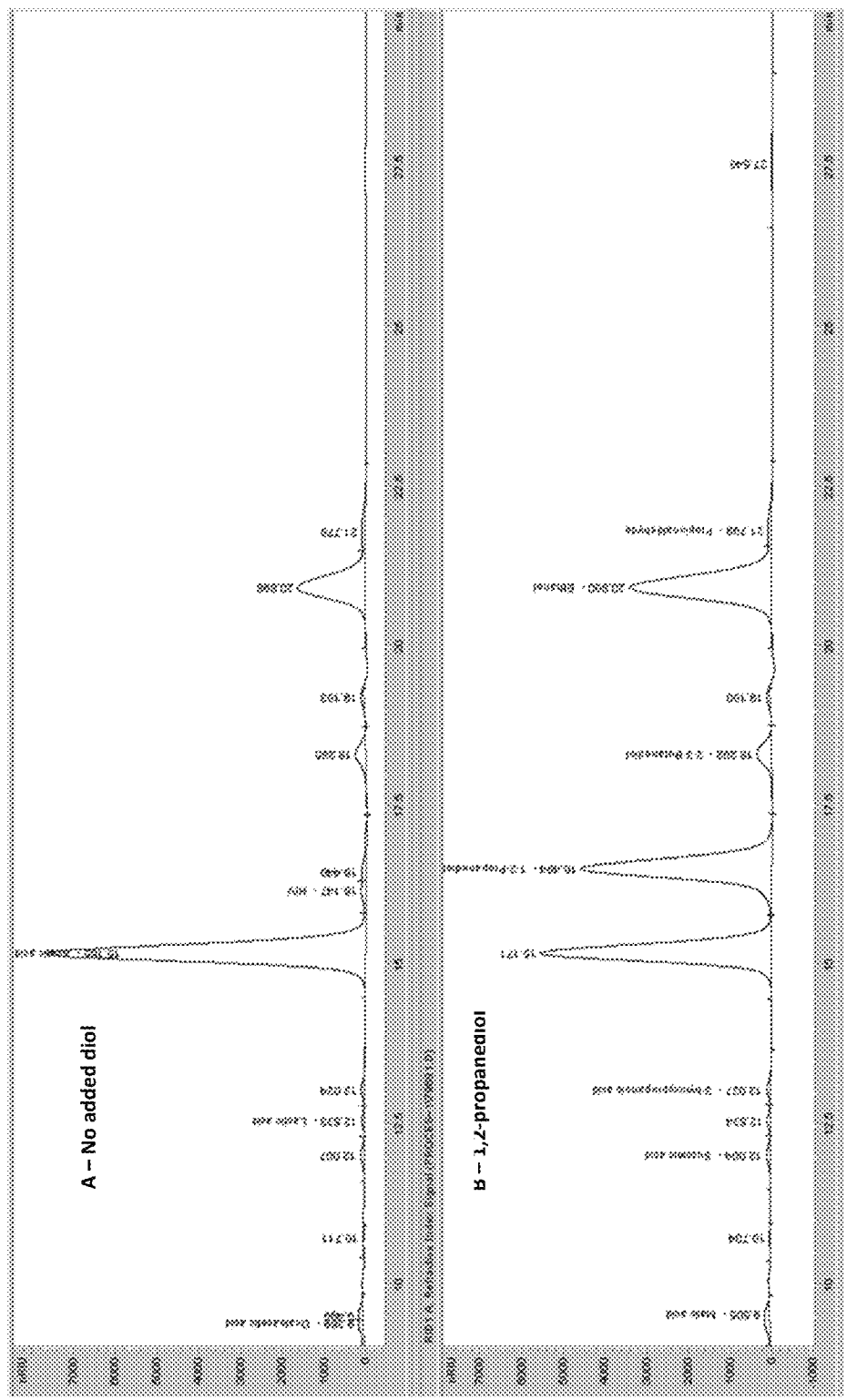
FIG. 11: HPLC chromatogram from cultures of C. autoethanogenum ClosTron mutant with inactivated diol dehydratase after 1 week of growth. Culture with no propane-1,2-diol added, A; and culture with (R)-propan-2-ol added, B, shows no conversion of propane-1,2-diol to propan-1-ol or propan-2-ol.

The pMTL007C-E2-pfl-1136-2052!2053s plasmid was introduced into *C. autoethanogenum* as described above. Streaks of single colonies on PETC-MES agar with 15 µg/ml thiamphenicol were made sequentially and 8 colonies were randomly screened for group II intron insertion by PCR using primers Og84f (SEQ ID NO:14) and Of85r (SEQ ID NO:15), flanking the group II intron insertion site in the target gene, and Maxime PCR PreMix Kit. 16s rDNA was also PCR amplified using primers fD1 (SEQ ID NO:16) and rP2 (SEQ ID NO:17) and Maxime PCR PreMix Kit. A PCR product of 316 bp indicates the unmodified wild type genotype and a PCR product of ~2 kb indicates insertion of group II intron in the target gene. All 8 clones appear positive for gene disruption as seen by the amplification of ~2 kb PCR product (FIG. 10). Further, sequencing of the PCR products from clones-4 (SEQ ID NO: 18 and 19) and -7 (SEQ ID NO: 20 and 21) confirmed the PCR products to be group II intron targeting fragment with RAM cassette. The 16s rDNA PCR products of clones-4 (SEQ ID NO: 22 and 23) and -7 (SEQ ID NO: 24 and 25) were also sequence verified which confirmed the two clones to be *C. autoethanogenum*. These results confirmed the disruption of a putative diol dehydratase gene in *C. autoethanogenum*. Clone 4 was tested by growth in the presence of propane-1,2-diol and the strain was unable to utilize propane-1,2-diol and form any propan-2-one, propan-2-ol, or propan-1-ol (FIG. 11), thus demonstrating that this enzyme represents the novel diol dehydratase responsible for stereospecific conversion of propane-1,2-diol into propan-2-one and propanal.

Figure 8:
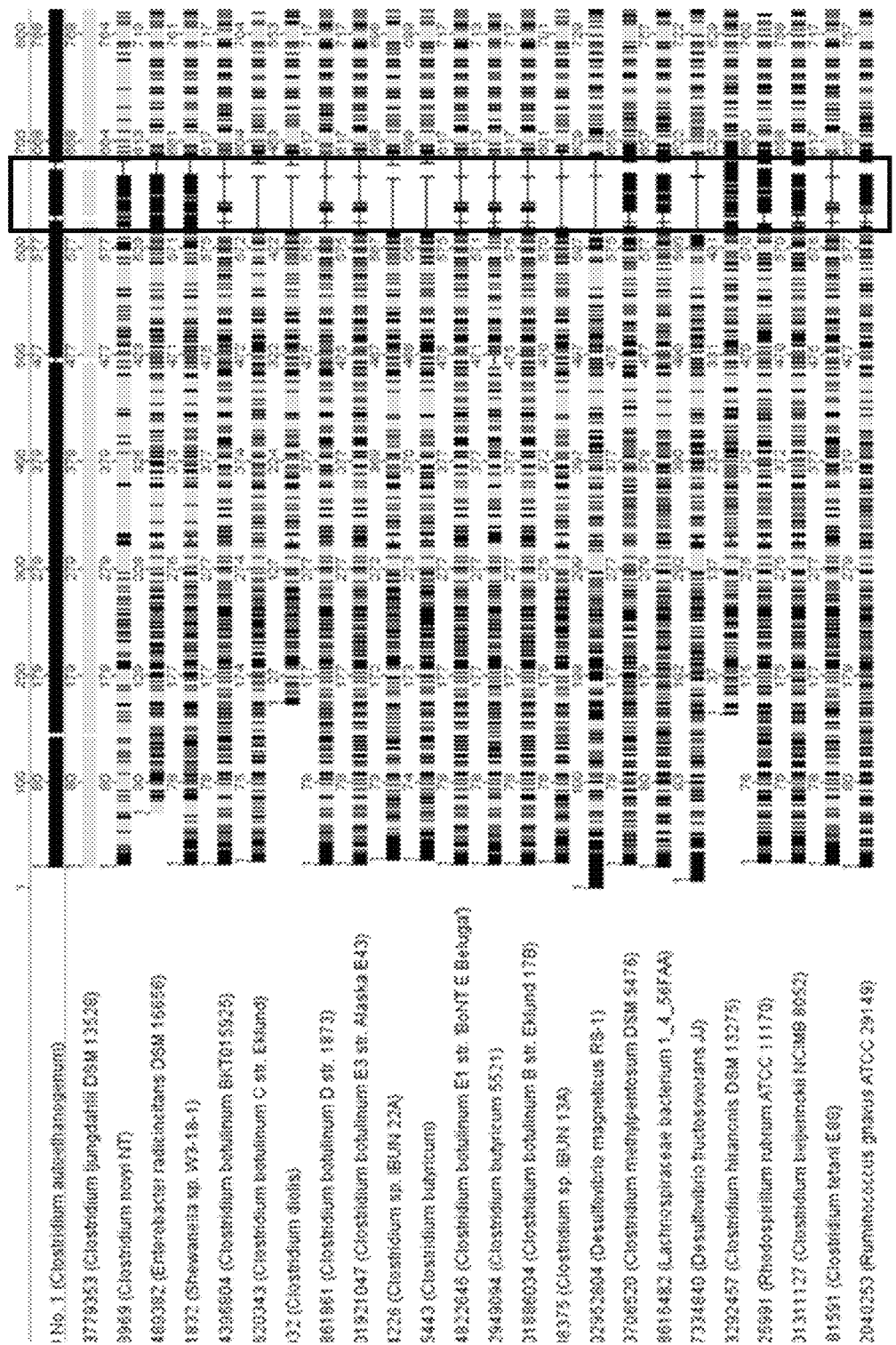
FIG. 8: Overview of alignment of diol dehydratase of C. autoethanogenum with most related enzymes from BLAST search. Grey bars represent identity to C. autoethanogenum reference sequence, while black areas represent mismatches and white areas represent gaps. A domain only present in C. autoethanogenum and C. ljungdahlii is highlighted in a box.

Similar genes (CLJU_c11830; 9444800 and CLJU_c11831; 9444801) and enzymes (YP_003779353 and YP_003779354) are only present in *C. ljungdahlii* with 99% (one mismatch), and 100% identity, respectively. The respective gene and enzyme is annotated as pyruvate:formate lyase, not as diol dehydratase. A BLAST result of the diol dehydratase enzyme (SEQ ID NO:1) is shown in Table 2, an overview in FIG. 8 (black bars are mismatches to the amino acids sequence of the reference *C. autoethanogenum* diol dehydratase, white areas represent gaps). It can be seen that there is a specific domain between position 596 and 656 (SEQ ID NO: 9) of the enzyme that is only present in *C. ljungdahlii* but not in any other enzymes, such as the known one from *C. butyricum*, while the rest of the enzyme shares good homology. Without being bound to this theory, the inventors believe that this protein domain may allow the conversion of propane-1,2-diol to propan-2-one and propanal.

To test if only the diol dehydratases of *C. autoethanogenum* and *C. ljungdahlii* can catalyze this novel reaction from propane-1,2-diol to propan-2-one and propanal, other carboxydotrophic organism as the closely related *C. ragsdalei* which share several features with *C. autoethanogenum* and *C. ljungdahlii* (Köpke et al. 2011) (WO 2008/028055) and organisms such as *C. butyricum* which have a related diol dehydratase were grown in presence of a racemix mix of 5 g/L propane-1,2-diol (Table 3). To ensure the glycerol/diol dehydratase gene was expressed, *C. butyricum* was grown in presence of glycerol.

TABLE 3

Conversion of propane-1,2-diol in carboxydotrophic organisms and organisms with known diol dehydratases and *E. coli*:

| Organism | Formation of propan-2-one/ propan-2-ol | Formation of propanal/ propan-1-ol |
| --- | --- | --- |
| *C. autoethanogenum* | Yes (stereospecific) | yes (stereospecific) |
| *C. ljungdahlii* | Yes | Yes |
| *C. ragsdalei* | No | No |
| *C. carboxidivorans* | No | Yes |
| *C. butyricum* | No | Yes |
| *E. coli* | No | No |
| *C. butyricum* (Brien et el. 2004) | No | Yes |
| *C. glucolicum* (Hartmanis and Stadtman 1986) | No | Yes |
| *K. pneumonia* (Toraya T, Shirakashi T, Kosuga T 1976) | No | Yes |

Figure 4:
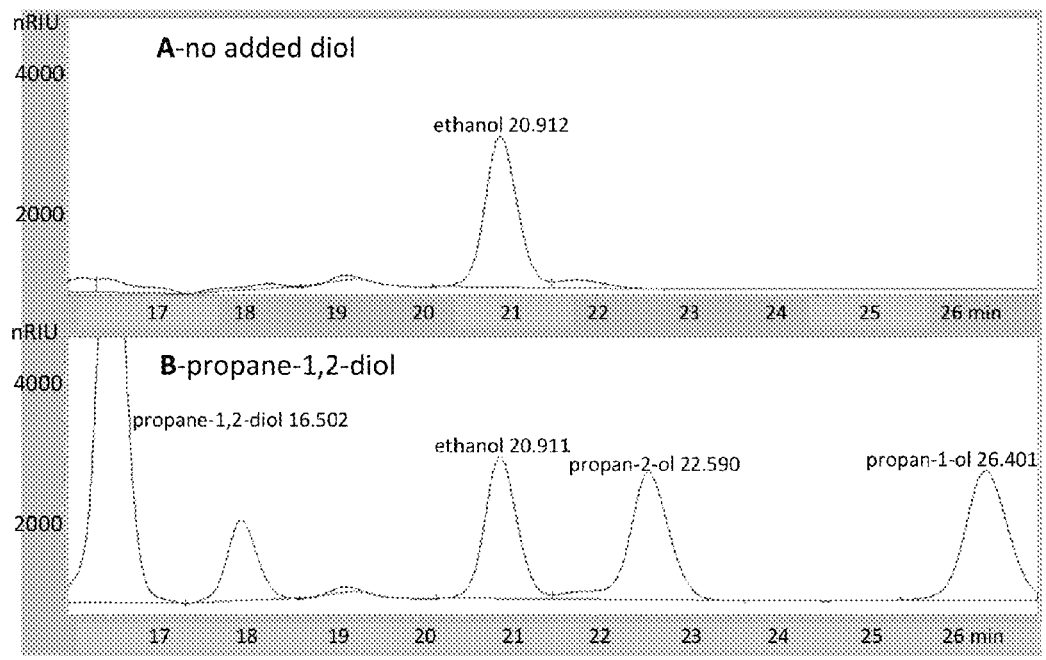
FIG. 4: HPLC chromatogram from cultures of C. ljungdahlii. Culture with no propane-1,2-diol added, A, shows no propan-1-ol or propan-2-ol; and culture with (R)-propan-2-ol added, B, shows production of propan-1-ol and propan-2-ol.
Figure 5:
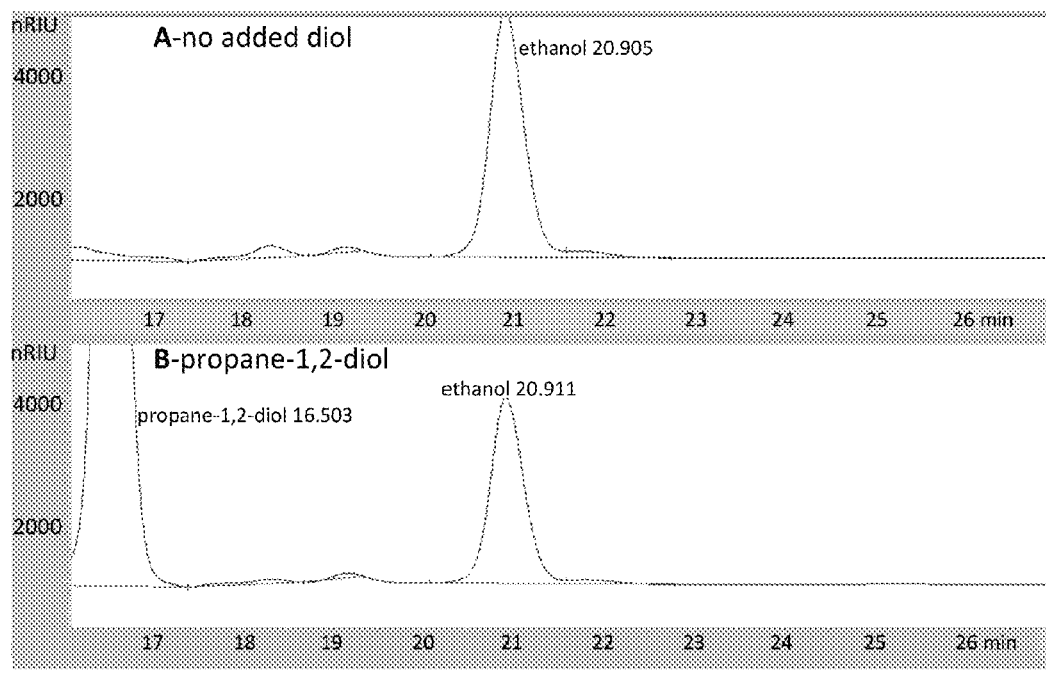
FIG. 5: HPLC chromatogram from cultures of C. ragsdalei. Culture with no propane-1,2-diol added, A; and culture with (R)-propan-2-ol added, B, shows no conversion of propane-1,2-diol to propan-1-ol or propan-2-ol
Figure 6:
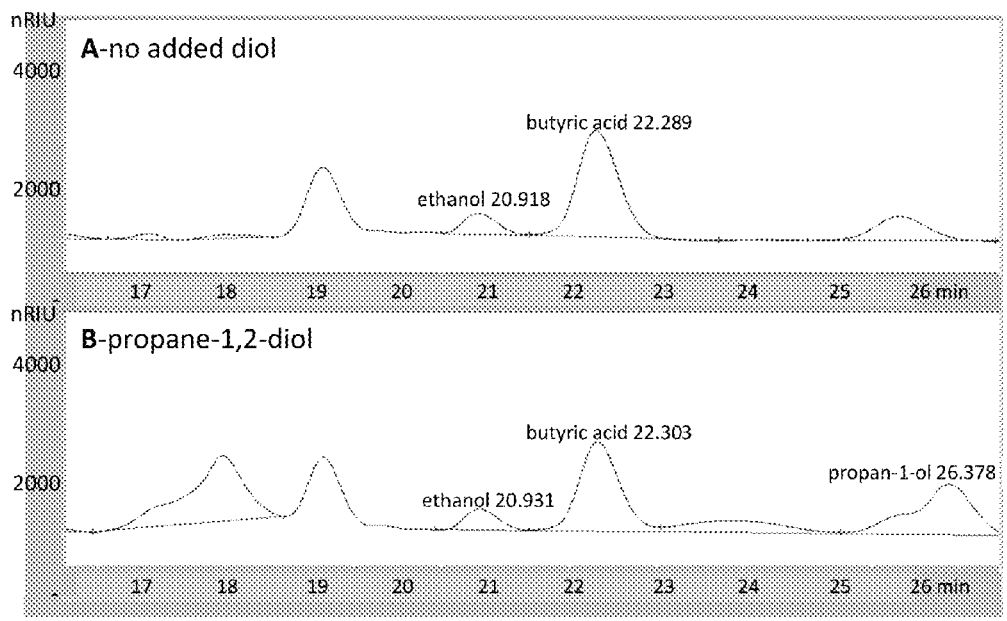
FIG. 6: HPLC chromatogram from cultures of C. carboxidivorans. Culture with no propane-1,2-diol added, A, shows no propan-1-ol or propan-2-ol; and culture with (R)-propan-2-ol added, B, shows no remaining propane-1,2-diol and production of only propan-1-ol and not propan-2-ol.
Figure 9:
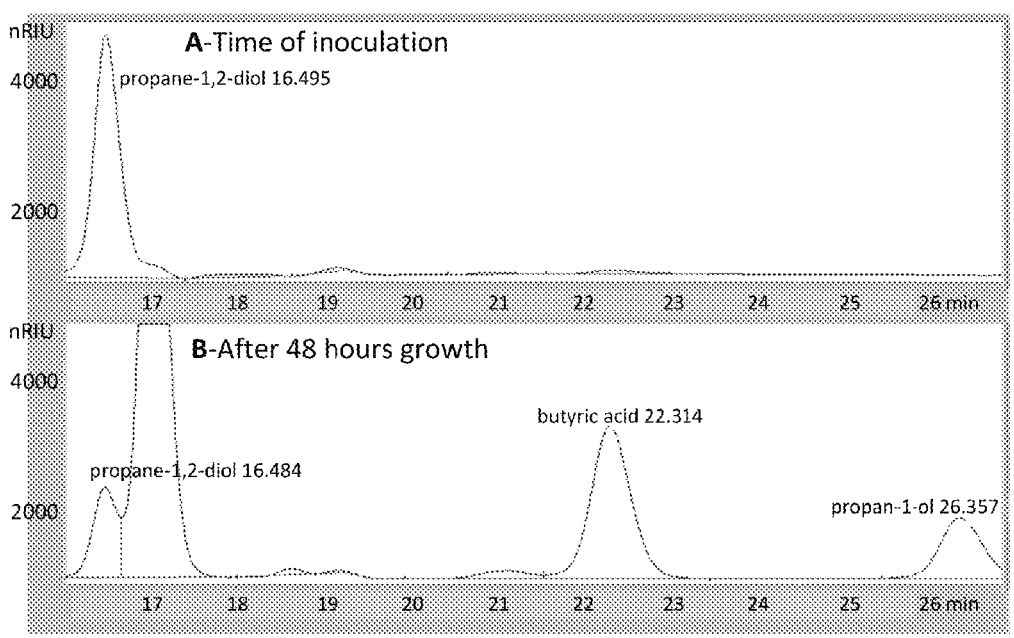
FIG. 9: HPLC chromatogram from cultures of C. butyricum. Culture at time of inoculation, A, shows glycerol and propane-1,2-diol. Culture after 48 hours of growth, B, shows some remaining propane-1,2-diol, and propan-1-ol produced.

*Clostridium ljungdahlii* cells indeed were able to convert racemic propane-1,2-diol to propan-1-ol and propan-2-ol because the same enzyme and also a secondary alcohol dehydrogenase are present (FIG. 4). *Clostridium ragsdalei* however showed no conversion or consumption of racemic propane-1,2-diol (FIG. 5). *Clostridium carboxidivorans* consumed all of the racemic propane-1,2-diol, but produced only propan-1-ol, but not propan-2-one or propan-2-ol (FIG. 6). *Clostridium butyricum* also converted the racemic propane-1,2-diol to propan-1-ol (FIG. 9) confirming results described in literature (Brien et al. 2004). For *Clostridium carboxidivorans*, conversion of propane-1,2-diol has not been observed before, but *Clostridium carboxidivorans* has genes for a dehydratase homologous to the vitamin B-12 dependent enzyme from *Klebsiella oxytoca*.

As described above, the diol dehydratase enzyme of *C. autoethanogenum* is stereospecific, converting the (S)-form and the (R)-form of propane-1,2-diol into different products. Cultures of *C. butyricum* were grown with the different stereo-isomers of propane-1,2-diol to determine if it had a similar stereospecificity. Propane-1,2-diol; racemic, (R), or (S), was added at 1 g L-1 (13 mM) at the time of inoculation. After 40 hours, the culture with (S)-propane-1,2-diol had converted all of the diol to propane-1-ol. The culture with racemic propane-1,2-diol had converted about 64% to propan-1-ol (8.3 mM). The Culture with (R)-propane-1,2-diol had converted about 19% to propan-1-ol (2.5 mM) (Table 4).

TABLE 4

Conversion of 1 g L-1 (13 mM) propane-1,2-diol isomers in *C. butyricum* after 40 hours of growth

| 1,2-PDO isomer | 1,2-PDO residual (mM) | Propan-1-ol produced (mM) | Propan-2-ol produced (mM) |
| --- | --- | --- | --- |
| None | 0 | 0 | 0 |
| Racemic | 3.9 | 8.3 | 0 |
| (R) | 11 | 2.5 | 0 |
| (S) | 0 | 13 | 0 |

The enzyme responsible for conversion of propane-1,2-ol in *C. butyricum* appears to convert the (S)-isomer at a greater rate than the (R)-isomer, however both isomers are converted to propan-1-al and reduced to propane-1-ol. This demonstrates that the enzyme of *C. butyricum* is a homologous diol dehydratase and not capable of a stereospecific conversion as the enzyme of *C. autoethanogenum*. Neither isomer is dehydrated by the *C. butyricum* enzyme to propan-2-one, as is observed in cultures of *C. autoethanogenum*.

Expression of a Heterologous Diol Dehydratase in *C. Autoethanogenum* to Increase Conversion Rate The promoter region of the phosphotransacetylase-acetate kinase operon (Ppta-ack) was amplified using primers Ppta-ack-NotI-F (SEQ ID NO: 10: GAGCGGCCGCAATAT-GATATTTATGTCC) and Ppta-ack-NdeI-R (SEQ ID NO: 11: TTCCATATGTTTCATGTTCATTTCCTCC) and cloned into the *E. coli-Clostridium* shuttle vector pMTL83151 (FJ797647.1) (Heap et al. 2009) using NotI and NdeI restriction sites, generating the plasmid pMTL83155. The genes encoding the diol dehydratase from *Klebsiella oxytoca*, pddABC were codon optimized (SEQ ID NO: 12) and synthesized. The synthesized pddABC operon was then subcloned into the pMTL83155 using restriction enzymes NdeI and EcoRI.

The plasmid, pMTL83155 pddABC was used to transform *C. autoethanogenum* using methods described above. Outgrowth was performed on YTF-agar hours the cells were scraped from the plate and suspended in 0.5 mL PBS and spread on YTF-agar (8 g/L tryptone, 5 g/L yeast extract, 2 g/L NaCl, 2.5 g/L fructose, and 7.5 g/L agar, pH 5.8) containing 15 μg mL$^{-1}$ thiamphenicol, and incubated at 37° C. in 30 psi Real Mill Gas. Single colonies were restreaked on PETC-MES-agar containing 15 μg mL$^{-1}$ thiamphenicol, then restreaked on PETC-MES-agar containing 15 μg mL$^{-1}$ thiamphenicol and 0.5% fructose. Multiple colonies were picked up from the plates with fructose and grown up in 3 mL of PETC-MES with 0.5% fructose in Balch tubes with 30 psi Real Mill Gas. Presence of plasmid was verified by PCR.

Figure 7:
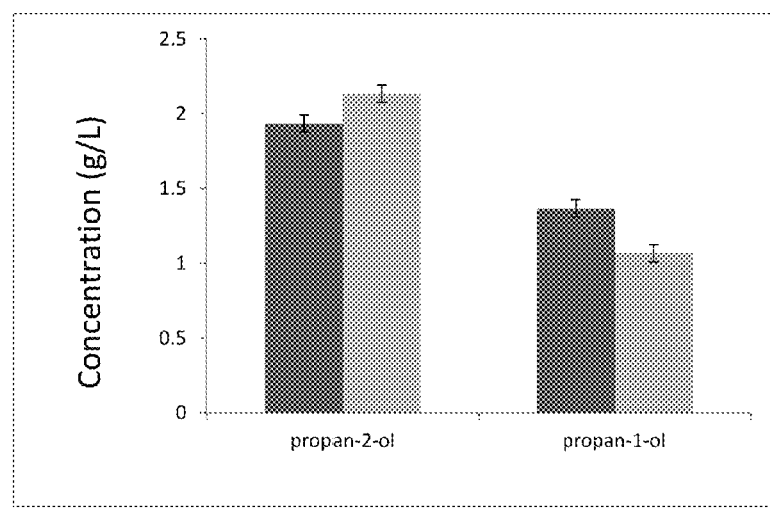
FIG. 7: Propanol production from propane-1,2-diol in C. autoethanogenum harbouring pMTL83155-pddABC, bars with solid outline; and in wildtype C. autoethanogenum, bars with broken outline. Error bars represent standard deviation of three replicates.

When *C. autoethanogenum* harbouring pMTL83155-pddABC was grown in the presence of propane-1,2-diol more propan-1-ol was produced than in the samples without the plasmid. The transgenic strain also produced less propan-2-ol than the wildtype (FIG. 7). These data indicate that the transgenic strain converted propane-1,2-diol to propan-1-ol at a faster rate than the wild type *C. autoethanogenum*.

Diol Dehydratase Activator Enzyme

The diol dehydratase from *C. butyricum* is understood to be a glycyl radical enzyme, requiring an activator enzyme to generate the radical through reductive cleavage of S-adenosylmethionine (Raynaud et al 2003, O'brien et al 2004). Other homologous enzymes with similar glycyl radical chemistries, such as pyruvate formate-lyase and anaerobic ribonucleotide reductase, have similar structures and activator enzymes (Atta et al, 2010). The diol dehydratase from *C. autoethanogenum* (SEQ ID NO: 1), having 59% identity to the *C. butyricum* diol dehydratase, is understood to have a similar structure and carry out similar chemistry for the dehydration of propane-1,2-diol. The gene (SEQ ID NO: 4) encoding the activator enzyme in *C. autoethanogenum* (SEQ ID NO: 2) is directly downstream of the diol dehydratase, as observed in *C. butyricum* and in the genes for pyruvate formate-lyase in *E. coli*.

Functional Expression of Diol Dehydratase and Activator Enzyme in *E. Coli*

To confirm identification of genes responsible for novel activity, and demonstrate that the enzymes function in alternative hosts, the genes encoding diol dehydratase (SEQ ID NO: 1) and activator enzyme (SEQ ID NO: 2) of *C. autoethanogenum* were expressed and demonstrated to function in *E. coli*. The genes (SEQ ID NO: 3-4) were synthesized with codons optimised for *E. coli* (SEQ ID NO: 26), and expressed in an operon on the plasmid pTrc99A (Amersham Pharmacia).

Figure 12:
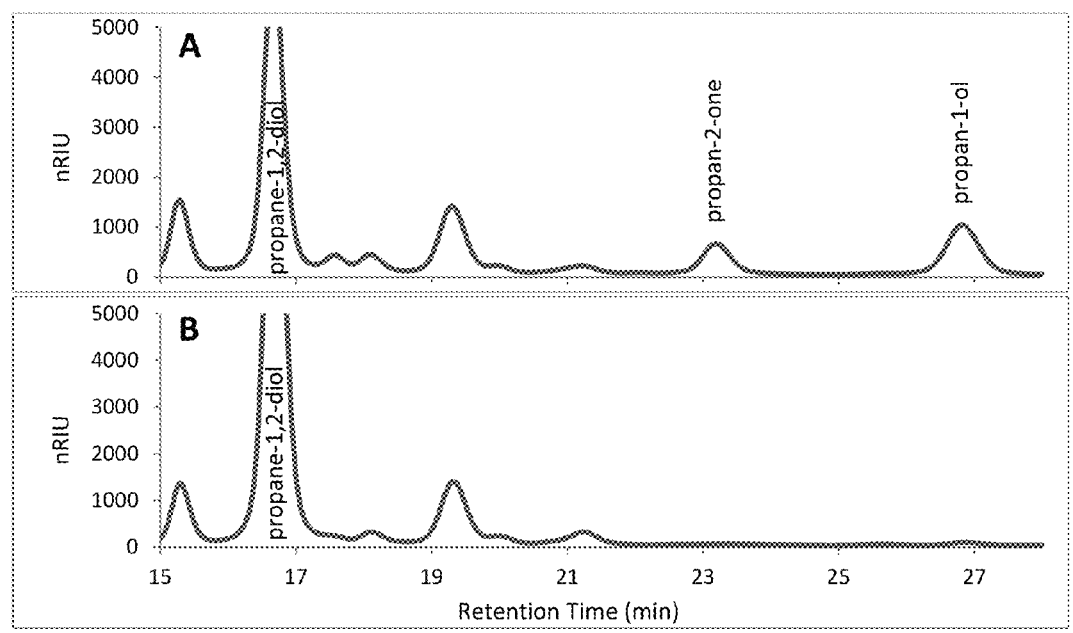
FIG. 12. HPLC chromatograms of culture broth from E. coli harbouring pTrc-dhaB1B2 (A) and pTrc99A (B) after 48 hours of growth in the presence of 4 g L-1 propane-1,2-diol.

*Escherichia coli* 1M109 was transformed with the constructed plasmid (pTrc-dhaB1B2) and with pTrc99A as a control. Overnight cultures grown in LB were used to inoculate 2×-YT supplemented with 0.2 mg/mL ferric ammonium sulphate dodecahydrate and containing 60 mM propane-1,2-diol (R, S, or racemic). After 4 hours of aerobic growth at 37° C. isopropyl β-D-1-thiogalactopyranoside was added to a final concentration of 1 mM to induce expression of the diol dehydratase and tubes were capped. The cultures were then grown at 30° C. After 48 hours the concentration of propane-1,2-diol and products were measured by HPLC (Table 5). In the case of racemic propane-1,2-diol the concentration of substrate had been reduced to 34 mM yielding 9.2 mM and 14.7 mM acetone (propane-2-one) and propan-1-ol respectively (FIG. 12). *Escherichia coli* lack a secondary alcohol dehydrogenase to reduce the propan-2-one to propan-2-ol as occurs in *C. autoethanogenum*. The propan-2-one was verified by GC to ensure it was not propan-2-ol which has a similar retention time on the HPLC method used.

TABLE 5

Stereospecific conversion of isomers of propane-1,2-diol by *E. coli* expressing diol dehydratase from *C. autoethanogenum*

| Isomer added | Residual diol (mM) | Acetone (mM) | 1-propanol (mM) |
|---|---|---|---|
| (R)-propane-1,2-diol | 24.5 | 32.9 | 3.7 |
| (S)-propane-1,2-diol | 47.7 | 0.0 | 16.7 |
| Racemic propane-1,2-diol | 34.3 | 9.2 | 14.7 |

This demonstrates successful conversion of propane-1,2-diol to propan-2-one and 1-propanol in recombinant *E. coli* expressing heterologous diol dehydratase operon of *C. autoethanogenum*.

A pathway for production of propane-1,2-diol production with *E. coli* has been described previously (Jain and Yan 2011). Expressing this pathway in combination with the diol dehydratase operon of *C. autoethanogenum* allows for production of acetone. Secondary alcohol dehydrogenase genes (as described in U.S. patent application Ser. No. 13/403,972 and U.S. Ser. No. 13/459,211) can be co-expressed for isopropanol production, while co-expressing genes described in (van Leeuwen et al. 2012) (WO2011032934) allow for isobutylene production.

The invention has been described herein, with reference to certain preferred embodiments, in order to enable the reader to practice the invention without undue experimentation. However, a person having ordinary skill in the art will readily recognise that many of the components and parameters may be varied or modified to a certain extent or substituted for known equivalents without departing from the scope of the invention. It should be appreciated that such modifications and equivalents are herein incorporated as if individually set forth. Titles, headings, or the like are provided to enhance the reader's comprehension of this document, and should not be read as limiting the scope of the present invention.

The entire disclosures of all applications, patents and publications, cited above and below, if any, are hereby incorporated by reference. However, the reference to any applications, patents and publications in this specification is not, and should not be taken as, an acknowledgment or any form of suggestion that they constitute valid prior art or form part of the common general knowledge in any country in the world.

Throughout this specification and any claims which follow, unless the context requires otherwise, the words "comprise," "comprising" and the like, are to be construed in an inclusive sense as opposed to an exclusive sense, that is to say, in the sense of "including, but not limited to."

We claim:

1. A recombinant microorganism comprising heterologous nucleic acids encoding (a) the stereospecific diol dehydratase of SEQ ID NO: 1, and (b) the activase of SEQ ID NO: 2.

2. A recombinant *Clostridium autoethanogenum* microorganism comprising nucleic acids encoding (a) the stereospecific diol dehydratase of SEQ ID NO: 1, and (b) the activase of SEQ ID NO: 2, wherein the microorganism has been genetically modified to increase the expression of the nucleic acids encoding the stereospecific diol dehydratase and activase compared to the unmodified wild-type *Clostridum autoethanogenum*.

3. A recombinant *Clostridium autoethanogenum* microorganism comprising nucleic acids encoding (a) the stereospecific diol dehydratase of SEQ ID NO: 1, and (b) the activase of SEQ ID NO: 2, wherein the microorganism has been genetically modified to increase the copy number of the nucleic acids encoding the stereospecific diol dehydratase and activase compared to the unmodified wild-type *Clostridum autoethanogenum*.

4. The microorganism of claim 1, wherein the microorganism produces one or more of propan-2-one, propan-2-ol, propanal, and propan-1-ol.

5. The microorganism of claim 1, wherein the microorganism further comprises an endogenous or exogenous alcohol dehydrogenase.

6. The microorganism of claim 5, wherein the alcohol dehydrogenase is a secondary alcohol dehydrogenase.

7. The microorganism of claim 2, wherein the microorganism further comprises a disruption in an endogenous alcohol dehydrogenase gene.

8. The microorganism of claim 7, wherein the alcohol dehydrogenase is a secondary alcohol dehydrogenase.

9. The microorganism of claim 2, wherein the microorganism produces one or more of propan-2-one, propan-2-ol, propanal, and propan-1-ol.

10. The microorganism of claim 2, wherein the microorganism further comprises an endogenous or exogenous alcohol dehydrogenase.

11. The microorganism of claim 10, wherein the alcohol dehydrogenase is a secondary alcohol dehydrogenase.

12. The microorganism of claim 3, wherein the microorganism comprises a disruption in an endogenous alcohol dehydrogenase gene.

13. The microorganism of claim 12, wherein the alcohol dehydrogenase is a secondary alcohol dehydrogenase.

14. A method of producing a product comprising culturing the microorganism of claim 1 in the presence of a substrate and propane-1,2-diol whereby the microorganism produces one or more of propan-2-one, propan-2-ol, propanal, and propan-1-ol.

15. The method of claim 14, wherein the propane-1,2-diol is one or both of (R)-propane-1,2-diol and (S)-propane-1,2-diol.

16. The method of claim 14, wherein the substrate comprises one or more of sugar, starch, cellulose, biomass, syngas, glycerol, and CO-containing gas.

17. A method of producing a product comprising culturing the microorganism of claim 2 in the presence of a substrate and propane-1,2-diol whereby the microorganism produces one or more of propan-2-one, propan-2-ol, propanal, and propan-1-ol.

18. The method of claim 17, wherein the propane-1,2-diol is one or both of (R)-propane-1,2-diol and (S)-propane-1,2-diol.

19. The method of claim 17, wherein the substrate comprises one or more of sugar, starch, cellulose, biomass, syngas, glycerol, and CO-containing gas.

* * * * *

SEQUENCE LISTING

<160> NUMBER OF SEQ ID NOS: 26

<210> SEQ ID NO 1
<211> LENGTH: 854
<212> TYPE: PRT
<213> ORGANISM: Clostridium autoethanogenum

<400> SEQUENCE: 1

```
Met Asn Asp Val Leu Asn Lys Leu Tyr Thr Ala Asn Gln Ser Lys Arg
 1               5                  10                  15

Ile Glu Lys Leu Thr Asn Asp Leu Tyr Ser Val Thr Pro Glu Ile Glu
            20                  25                  30

Ala Gln Arg Ala Val Leu Ile Thr Glu Ser Phe Lys Glu Thr Glu Ala
        35                  40                  45

Tyr Pro Met Ile Ile Arg Arg Ala Lys Ala Leu Glu Lys Ile Leu Asn
    50                  55                  60

Glu Met Asp Ile Val Ile Arg Asp Glu Glu Leu Ile Val Gly Asn Leu
65                  70                  75                  80

Thr Lys Lys Pro Arg Ala Ala Ser Ile Phe Pro Glu Phe Ser Asn Lys
                85                  90                  95

Trp Leu Leu Glu Glu Phe Asp Thr Leu Ala Lys Arg Thr Gly Asp Val
            100                 105                 110

Phe Leu Ile Ser Glu Asp Val Lys Ser Gln Leu Arg Glu Val Phe Lys
        115                 120                 125

Tyr Trp Asp Gly Lys Thr Thr Asn Glu Leu Ala Thr Glu Tyr Met Phe
    130                 135                 140

Ser Glu Thr Lys Glu Ala Met Glu Ala Gly Val Phe Thr Val Gly Asn
145                 150                 155                 160

Tyr Tyr Phe Asn Gly Ile Gly His Ile Ser Val Asp Tyr Ala Lys Val
                165                 170                 175

Leu Ser Lys Gly Phe Asn Gly Ile Ile Glu Asp Ala Glu Ser Glu Lys
            180                 185                 190

Ala Lys Ala Asp Lys Ala Asp Pro Asp Tyr Ile Lys Lys Asp Gln Phe
        195                 200                 205

Leu Thr Ala Val Ile Ile Thr Ser Lys Ala Val Ile Lys Phe Ala Arg
    210                 215                 220

Arg Phe Ala Glu Leu Ala Arg Asn Leu Ala Ser Gln Ser Leu Asp Ser
225                 230                 235                 240

Arg Arg Arg Glu Glu Leu Met Gln Ile Ala Glu Asn Cys Gln Trp Val
                245                 250                 255

Pro Glu Arg Pro Ala Arg Thr Phe Tyr Glu Ala Leu Gln Ser Phe Trp
            260                 265                 270

Phe Val Gln Ser Ile Ile Gln Ile Glu Ser Asn Gly His Ser Ile Ser
        275                 280                 285

Pro Met Arg Phe Asp Gln Tyr Met Tyr Pro Tyr Phe Lys Lys Asp Val
    290                 295                 300

Ser Asn Gly Leu Ile Thr Gln Glu Lys Ala Gln Glu Leu Leu Asp Cys
305                 310                 315                 320

Leu Trp Val Lys Phe Asn Asp Val Asn Lys Val Arg Asp Glu Gly Ser
                325                 330                 335

Thr Lys Ala Phe Gly Gly Tyr Pro Met Phe Gln Asn Leu Ile Val Gly
            340                 345                 350

Gly Gln Thr Ile Asp Gly Arg Asp Ala Thr Asn Glu Leu Ser Phe Met
        355                 360                 365
```

-continued

```
Cys Leu Glu Ala Thr Ala His Thr Lys Leu Pro Gln Pro Ser Ile Ser
    370                 375                 380

Ile Arg Ala Trp Asn Lys Thr Pro Asp Glu Leu Leu Lys Ala Ala
385                 390                 395                 400

Glu Val Thr Arg Leu Gly Leu Gly Met Pro Ala Tyr Tyr Asn Asp Glu
                405                 410                 415

Val Ile Ile Pro Ser Leu Thr Ser Arg Gly Leu Thr Leu Glu Asp Ala
            420                 425                 430

Arg Asp Tyr Gly Ile Ile Gly Cys Val Glu Pro Gln Lys Gly Gly Lys
            435                 440                 445

Thr Glu Gly Trp His Asp Ala Ala Phe Phe Asn Ile Val Lys Val Leu
450                 455                 460

Glu Ile Thr Ile Asn Asn Gly Met Asp Asn Gly Lys Gln Ile Gly Leu
465                 470                 475                 480

Arg Thr Gly Asp Phe Thr Ser Phe Thr Ser Phe Glu Lys Leu Phe Asp
                485                 490                 495

Ala Tyr Lys Leu Gln Met Glu Tyr Phe Val Lys Leu Leu Val Asn Ala
                500                 505                 510

Asp Asn Ser Val Asp Leu Ala His Gly Glu Arg Ala Pro Leu Pro Phe
            515                 520                 525

Leu Ser Ser Met Ala Asp Asp Cys Ile Ala Arg Gly Lys Ser Leu Gln
530                 535                 540

Glu Gly Gly Ala His Tyr Asn Phe Thr Gly Pro Gln Gly Val Gly Val
545                 550                 555                 560

Ala Asn Ala Ala Asp Ser Leu Glu Ala Ile Lys Lys Leu Val Phe Glu
                565                 570                 575

Asp Lys Lys Ile Thr Leu Gln Asp Leu Lys Asn Ala Leu Asp Thr Asn
                580                 585                 590

Phe Gly Glu Cys Lys Lys Asn Pro Ile Ser Glu Leu Ala Asn Ser Ile
                595                 600                 605

Asn Glu Val Gly Asp Met Lys Gly Leu Thr Pro Glu Thr Ile Leu Lys
            610                 615                 620

Val Ile Glu Lys Leu Leu Ser Glu Glu Lys Lys Thr Ser Leu Glu Gly
625                 630                 635                 640

Leu Glu Pro Gly Lys Asp Ile Asn Leu Gly Ser Tyr Gly Asn Lys Glu
                645                 650                 655

Ser Ile Arg Gln Met Leu Leu Asn Arg Ala Pro Lys Phe Gly Asn Asp
            660                 665                 670

Ile Asp Glu Val Asp Asp Leu Ala Arg Glu Ala Ala Leu Ile Tyr Cys
            675                 680                 685

Asn Glu Val Glu Lys Tyr Thr Asn Pro Arg Asn Gly Gln Phe Gln Pro
            690                 695                 700

Gly Leu Tyr Pro Val Ser Ala Asn Val Pro Met Gly Ser Gln Thr Gly
705                 710                 715                 720

Ala Thr Pro Asp Gly Arg Lys Ala Gly Glu Pro Leu Ala Asp Gly Val
                725                 730                 735

Ser Pro Val Ser Gly Arg Asp Ala Met Gly Pro Thr Ala Ala Ala Asn
            740                 745                 750

Ser Val Ala Lys Ile Asp His Cys Lys Ala Ser Asn Gly Thr Leu Phe
            755                 760                 765

Asn Gln Lys Phe His Pro Ser Ala Leu Glu Gly Gln Thr Gly Leu Gln
770                 775                 780
```

```
Asn Leu Ser Ser Leu Val Arg Thr Phe Phe Asp Glu Lys Gly Leu His
785                 790                 795                 800

Val Gln Phe Asn Val Val Ser Arg Glu Thr Leu Leu Asp Ala Gln Lys
            805                 810                 815

Asn Pro Glu Asn Tyr Arg Asn Leu Val Val Arg Val Ala Gly Tyr Ser
            820                 825                 830

Ala His Phe Thr Ser Leu Asp Lys Ser Ile Gln Asp Ile Ile Lys
        835                 840                 845

Arg Thr Glu His Thr Phe
    850

<210> SEQ ID NO 2
<211> LENGTH: 259
<212> TYPE: PRT
<213> ORGANISM: Clostridium autoethanogenum

<400> SEQUENCE: 2

Met Glu Pro Gln Val Met Phe Ile Pro Ser Lys Cys Ile Gly Cys Lys
1               5                   10                  15

Lys Cys Tyr Glu Val Cys Ser Asn Gly Ala Ile Asp Phe Asn Leu Pro
            20                  25                  30

Ser Arg Val Asp Gln Asn Lys Cys Val Lys Cys Gly Lys Cys Val Glu
        35                  40                  45

Asn Cys Tyr Ala Gly Ala Leu Asn Leu Ala Gly Asn Thr Arg Thr Val
50                  55                  60

Lys Glu Leu Leu Leu Glu Leu Lys Lys Asp Asn Ile Tyr Tyr Arg Arg
65                  70                  75                  80

Ser Gly Gly Gly Ile Thr Leu Ser Gly Glu Val Thr Ala Gln Pro
                85                  90                  95

Glu Phe Ala Glu Glu Leu Leu Lys Gly Cys Lys Gln Asn Gly Trp His
            100                 105                 110

Thr Ala Ile Glu Thr Ala Ala Phe Thr Ser Gln Ser Val Leu Glu Arg
        115                 120                 125

Met Leu Pro Trp Leu Asp Leu Val Met Leu Asp Ile Lys His Met Asp
130                 135                 140

Ala Asn Lys His Leu Glu Tyr Thr Gly Lys Pro Asn Glu Leu Ile Leu
145                 150                 155                 160

Gln Asn Ala Lys Leu Ile Ala Gln Phe Gly Val Gln Leu Ile Ile Arg
            165                 170                 175

Val Pro Val Ile Pro Gly Val Asn Ser Asp Glu Asn Asn Ile Arg Ala
        180                 185                 190

Thr Ala Asn Phe Ala Thr Ser Leu Lys Ser Val Lys Glu Leu His Leu
    195                 200                 205

Leu Pro Tyr His Arg Leu Gly Glu Asn Lys Tyr Glu Tyr Leu Gly His
210                 215                 220

Asp Tyr Ile Met Lys Gly Leu Gln Pro Pro Thr Lys Glu Glu Ile Asn
225                 230                 235                 240

Lys Leu Lys Glu Leu Val Glu Glu Cys Gly Leu Ile Cys Lys Val Gly
            245                 250                 255

Gly Ile Asp

<210> SEQ ID NO 3
<211> LENGTH: 2565
<212> TYPE: DNA
<213> ORGANISM: Clostridium autoethanogenum
```

```
<400> SEQUENCE: 3
ttgaatgatg tttaaacaa actttatact gcaaatcaaa gtaaaagaat agaaaaatta      60
actaacgatt tatactcggt aactcctgaa atcgaagcgc aaagagcagt tttaataacg     120
gaatctttta aggaaactga agcttatcct atgattatta agagctaa agctttagaa      180
aaaatactaa atgaaatgga tatagttatt cgtgatgaag aacttattgt aggaaattta    240
actaaaaaac ctagagcggc ttcaatattt ccggaatttt caataagtg gcttttggag     300
gaatttgata ctcttgcaaa agaactggt gatgtatttc ttattagtga agatgtaaaa    360
tcacaactta gagaagtatt caaatattgg gatggaaaaa caacaaatga gcttgcaaca   420
gagtatatgt tttcagaaac gaaggaagca atggaagcag gggtatttac tgttggaaat    480
tattacttca atggtatagg tcatatttct gtagattatg caaaagtatt atctaaagga   540
tttaacggta taattgaaga tgcagaaagt gaaaaggcta aagcagataa agcagatcca   600
gattacataa agaaggatca gttttttaaca gctgtaatca taacttcaaa agctgttatt   660
aagtttgcta gacgttttgc tgaattagct agaaatttag caagtcaatc attggattca   720
cgaagacgtg aagagttaat gcaaatagct gaaaattgtc agtgggtacc tgaaagacca    780
gctagaacgt tttatgaggc tctacaatca ttttggtttg tacaatctat tattcaaata   840
gaatctaatg gacattcaat atcacctatg cgttttgacc aatacatgta tccttatttt    900
aagaaggatg tatcaaatgg acttattaca caagaaaaag cccaagaact tttagattgt   960
ctatgggtta aatttaatga tgttaataag gttcgtgatg aaggatcaac aaaagcattt   1020
ggtggatatc caatgttcca gaacttaatt gtaggtggac aaactattga tggaagagat   1080
gctacaaatg agctttcatt tatgtgcctt gaagctactg cacataccaa attaccgcaa   1140
ccatcaattt caataagagc ttggaacaaa actccagatg agttattatt aaaagctgct   1200
gaagtaactc gtttaggttt aggtatgcca gcttactata tgatgaagt tatcattcct    1260
tctttgacaa gccgcggtct tacgttagaa gatgctagag attatggtat tattggatgt   1320
gtagaacctc aaaaggtgg aaagacggaa ggatggcatg atgctgcatt ctttaatatt    1380
gtaaaggtat tagagataac tataaataat ggtatggata atggcaaaca gataggatta   1440
agaactggag acttcacttc ttttacatca tttgagaaat tatttgatgc atacaaatta    1500
cagatggagt attttgttaa actttagtt aatgcagata acagtgtaga tttagcacat    1560
ggagagagag caccattacc attcttatct tcaatggcag acgattgtat agctagagga   1620
aagtcattac aagaaggagg agcacattac aactttacag gaccacaagg agtaggagtt    1680
gcaaatgcag cagactcgtt agaagctatt aagaaacttg ttttttgaaga taagaagata   1740
actttcagg atttaaagaa tgcgttagac actaattttg gtgaatgtaa gaaaaaccca    1800
atatctgaac ttgctaatag cataaatgaa gtgggtgata tgaaaggatt aacacctgaa   1860
actatattga aagttattga gaaattatta tcagaagaaa agaaaacctc attagaagga    1920
ttggagccgg gtaaagatat taatttaggt agttatggaa ataaagagag tattcgtcaa   1980
atgctattaa atagagcacc taagtttggt aatgatatag atgaggttga tgatttagca   2040
cgagaagccg cattaattta ctgtaatgaa gttgaaaaat acactaatcc acgtaatggt    2100
caattccaac caggacttta tcctgttct gcaaatgttc aatgggatc acagacagga    2160
gcaacaccag atggaagaaa agctggggaa ccactagcag atggtgtatc accagtttca    2220
ggaagagatg caatgggacc aactgcagct gctaattctg ttgcgaaaat agaccattgt    2280
aaagcttcaa atggtacatt atttaatcaa aagttttcatc catctgcttt agaaggtcag    2340
```

```
actggtttac agaatttatc ttctctagta agaaccttt  tcgatgaaaa aggattacat    2400
gtacaattta atgtagtaag tagagaaacg cttttagatg ctcaaaagaa tcctgaaaat    2460
tatagaaatc tggtagtacg tgtagccgga tatagtgctc actttacttc tttagataag    2520
tcaattcagg atgatattat aaaaagaaca gaacatactt tttag                    2565

<210> SEQ ID NO 4
<211> LENGTH: 780
<212> TYPE: DNA
<213> ORGANISM: Clostridium autoethanogenum

<400> SEQUENCE: 4
atggagccac aagtaatgtt tattccaagc aaatgtatag gatgtaaaaa atgctatgaa      60
gtttgcagta atgagcaat agatttcaac cttccttcta gagttgatca gaataaaatgt    120 gttaagtgtg gtaagtgtgt tgagaattgt tatgctggag ctttgaattt agcaggaaac    180
acgagaactg taaggaatt gttactagaa ttgaaaaagg ataacatata ttatagacga    240
tctggtggtg gaattacttt atcaggagga gaagtaacag ctcaacctga gtttgctgaa    300
gaattactaa aaggatgcaa acaaaatggt tggcacacag ctattgaaac cgcagcattt    360
acatctcaaa gtgttttaga aaggatgcta ccttggcttg atttagttat gcttgatatt    420
aagcacatgg atgcaaataa acatttagag tatacaggaa agcctaatga gttaatctta    480
cagaatgcaa aattaatagc tcagtttgga gttcagttaa taataagagt acctgttatt    540
ccaggagtta atagcgatga aataatata gagctacag ctaattttgc aactagcctt    600
aaaagtgtta agaattaca tcttctacca taccatcgtc ttggtgaaaa taagtatgag    660
tacttaggac atgattatat aatgaagggt ttacaaccac ctactaaaga agaaataaat    720
aagcttaaag aactagtgga agaatgtgga ctaatatgta agttggtgg aattgactag    780

<210> SEQ ID NO 5
<211> LENGTH: 351
<212> TYPE: PRT
<213> ORGANISM: Clostridium autoethanogenum

<400> SEQUENCE: 5

Met Lys Gly Phe Ala Met Leu Gly Ile Asn Lys Leu Gly Trp Ile Glu
1               5                   10                  15

Lys Lys Asn Pro Val Pro Gly Pro Tyr Asp Ala Ile Val His Pro Leu
            20                  25                  30

Ala Val Ser Pro Cys Thr Ser Asp Ile His Thr Val Phe Glu Gly Ala
        35                  40                  45

Leu Gly Asn Arg Glu Asn Met Ile Leu Gly His Glu Ala Val Gly Glu
    50                  55                  60

Ile Ala Glu Val Gly Ser Glu Val Lys Asp Phe Lys Val Gly Asp Arg
65                  70                  75                  80

Val Ile Val Pro Cys Thr Thr Pro Asp Trp Arg Ser Leu Glu Val Gln
                85                  90                  95

Ala Gly Phe Gln Gln His Ser Asn Gly Met Leu Ala Gly Trp Lys Phe
            100                 105                 110

Ser Asn Phe Lys Asp Gly Val Phe Ala Asp Tyr Phe His Val Asn Asp
        115                 120                 125

Ala Asp Met Asn Leu Ala Ile Leu Pro Asp Glu Ile Pro Leu Glu Ser
    130                 135                 140

Ala Val Met Met Thr Asp Met Thr Thr Gly Phe His Gly Ala Glu
145                 150                 155                 160
```

```
Leu Ala Asp Ile Lys Met Gly Ser Ser Val Val Ile Gly Ile Gly
            165                 170                 175
Ala Val Gly Leu Met Gly Ile Ala Gly Ser Lys Leu Arg Gly Ala Gly
        180                 185                 190
Arg Ile Ile Gly Val Gly Ser Arg Pro Val Cys Val Glu Thr Ala Lys
        195                 200                 205
Phe Tyr Gly Ala Thr Asp Ile Val Asn Tyr Lys Asn Gly Asp Ile Val
        210                 215                 220
Glu Gln Ile Met Asp Leu Thr His Gly Lys Val Asp Arg Val Ile
225                 230                 235                 240
Met Ala Gly Gly Ala Glu Thr Leu Ala Gln Ala Val Thr Met Val
                245                 250                 255
Lys Pro Gly Gly Val Ile Ser Asn Ile Asn Tyr His Gly Ser Gly Asp
        260                 265                 270
Thr Leu Pro Ile Pro Arg Val Gln Trp Gly Cys Gly Met Ala His Lys
        275                 280                 285
Thr Ile Arg Gly Gly Leu Cys Pro Gly Gly Arg Leu Arg Met Glu Met
        290                 295                 300
Leu Arg Asp Leu Val Leu Tyr Lys Arg Val Asp Leu Ser Lys Leu Val
305                 310                 315                 320
Thr His Val Phe Asp Gly Ala Glu Asn Ile Glu Lys Ala Leu Leu Leu
                325                 330                 335
Met Lys Asn Lys Pro Lys Asp Leu Ile Lys Ser Val Val Thr Phe
                340                 345                 350
```

<210> SEQ ID NO 6
<211> LENGTH: 1056
<212> TYPE: DNA
<213> ORGANISM: Clostridium autoethanogenum

<400> SEQUENCE: 6

```
atgaaaggtt ttgcaatgtt aggtattaac aaattaggat ggattgaaaa gaaaaaccca      60
gtgccaggtc cttatgatgc gattgtacat cctctagctg tatccccatg tacatcagat     120
atacatacgg tttttgaagg agcacttggt aatagggaaa atatgatttt aggccatgaa     180
gctgtaggtg aaatagccga agttggcagc gaagttaaag attttaaagt tggcgataga     240
gttatcgtac catgcacaac acctgactgg agatctttag aagtccaagc tggttttcag     300
cagcattcaa acggtatgct tgcaggatgg aagttttcca attttaaaga tggtgtattt     360
gcagattact tcatgtaaa cgatgcagat atgaatcttg ccatactccc agatgaaata     420
ccttagaaa gtgcagttat gatgacagac atgatgacta ctggttttca tggagcagaa     480
cttgcagaca taaaaatggg ctccagcgtt gtagtaattg gtataggagc tgttggatta     540
atgggaatag ccggttccaa acttcgagga gcaggcagaa ttatcggtgt tggaagcaga     600
cctgtttgtg ttgaaacagc taaatttat ggagcaactg atattgtaaa ttataaaaat     660
ggtgatatag ttgaacaaat catggactta actcatggta aggtgtaga ccgtgtaatc     720
atggcaggcg gtggtgctga aacactagca caagcagtaa ctatggttaa acctggcggc     780
gtaatttcta acatcaacta ccatggaagc ggtgatactt taccaatacc tcgtgttcaa     840
tggggctgcg gcatggctca aaaactata agaggaggat tatgccccgg cggacgtctt     900
agaatggaaa tgctaagaga tcttgttcta tataaacgtg ttgatttgag taaacttgtt     960
actcatgtat ttgatggtgc agaaaatatt gaaaaggccc ttttgcttat gaaaaataag    1020
ccaaaagatt taattaaatc agtagttaca ttctaa                              1056
```

<210> SEQ ID NO 7
<211> LENGTH: 601
<212> TYPE: PRT
<213> ORGANISM: Artificial Sequence
<220> FEATURE:
<223> OTHER INFORMATION: designed type II methyltransferase

<400> SEQUENCE: 7

```
Met Phe Pro Cys Asn Ala Tyr Ile Glu Tyr Gly Asp Lys Asn Met Asn
 1               5                  10                  15

Ser Phe Ile Glu Asp Val Glu Gln Ile Tyr Asn Phe Ile Lys Lys Asn
            20                  25                  30

Ile Asp Val Glu Glu Lys Met His Phe Ile Glu Thr Tyr Lys Gln Lys
        35                  40                  45

Ser Asn Met Lys Lys Glu Ile Ser Phe Ser Glu Glu Tyr Tyr Lys Gln
    50                  55                  60

Lys Ile Met Asn Gly Lys Asn Gly Val Val Tyr Thr Pro Pro Glu Met
65                  70                  75                  80

Ala Ala Phe Met Val Lys Asn Leu Ile Asn Val Asn Asp Val Ile Gly
                85                  90                  95

Asn Pro Phe Ile Lys Ile Ile Asp Pro Ser Cys Gly Ser Gly Asn Leu
            100                 105                 110

Ile Cys Lys Cys Phe Leu Tyr Leu Asn Arg Ile Phe Ile Lys Asn Ile
        115                 120                 125

Glu Val Ile Asn Ser Lys Asn Asn Leu Asn Leu Lys Leu Glu Asp Ile
    130                 135                 140

Ser Tyr His Ile Val Arg Asn Asn Leu Phe Gly Phe Asp Ile Asp Glu
145                 150                 155                 160

Thr Ala Ile Lys Val Leu Lys Ile Asp Leu Phe Leu Ile Ser Asn Gln
                165                 170                 175

Phe Ser Glu Lys Asn Phe Gln Val Lys Asp Phe Leu Val Glu Asn Ile
            180                 185                 190

Asp Arg Lys Tyr Asp Val Phe Ile Gly Asn Pro Pro Tyr Ile Gly His
        195                 200                 205

Lys Ser Val Asp Ser Ser Tyr Ser Tyr Val Leu Arg Lys Ile Tyr Gly
    210                 215                 220

Ser Ile Tyr Arg Asp Lys Gly Asp Ile Ser Tyr Cys Phe Phe Gln Lys
225                 230                 235                 240

Ser Leu Lys Cys Leu Lys Glu Gly Gly Lys Leu Val Phe Val Thr Ser
                245                 250                 255

Arg Tyr Phe Cys Glu Ser Cys Ser Gly Lys Glu Leu Arg Lys Phe Leu
            260                 265                 270

Ile Glu Asn Thr Ser Ile Tyr Lys Ile Ile Asp Phe Tyr Gly Ile Arg
        275                 280                 285

Pro Phe Lys Arg Val Gly Ile Asp Pro Met Ile Ile Phe Leu Val Arg
    290                 295                 300

Thr Lys Asn Trp Asn Asn Asn Ile Glu Ile Ile Arg Pro Asn Lys Ile
305                 310                 315                 320

Glu Lys Asn Glu Lys Asn Lys Phe Leu Asp Ser Leu Phe Leu Asp Lys
                325                 330                 335

Ser Glu Lys Cys Lys Lys Phe Ser Ile Ser Gln Lys Ser Ile Asn Asn
            340                 345                 350

Asp Gly Trp Val Phe Val Asp Glu Val Glu Lys Asn Ile Ile Asp Lys
        355                 360                 365
```

```
Ile Lys Glu Lys Ser Lys Phe Ile Leu Lys Asp Ile Cys His Ser Cys
370                 375                 380

Gln Gly Ile Ile Thr Gly Cys Asp Arg Ala Phe Ile Val Asp Arg Asp
385                 390                 395                 400

Ile Ile Asn Ser Arg Lys Ile Glu Leu Arg Leu Ile Lys Pro Trp Ile
                405                 410                 415

Lys Ser Ser His Ile Arg Lys Asn Glu Val Ile Lys Gly Glu Lys Phe
                420                 425                 430

Ile Ile Tyr Ser Asn Leu Ile Glu Asn Glu Thr Glu Cys Pro Asn Ala
            435                 440                 445

Ile Lys Tyr Ile Glu Gln Tyr Lys Lys Arg Leu Met Glu Arg Arg Glu
450                 455                 460

Cys Lys Lys Gly Thr Arg Lys Trp Tyr Glu Leu Gln Trp Gly Arg Lys
465                 470                 475                 480

Pro Glu Ile Phe Glu Glu Lys Lys Ile Val Phe Pro Tyr Lys Ser Cys
                485                 490                 495

Asp Asn Arg Phe Ala Leu Asp Lys Gly Ser Tyr Phe Ser Ala Asp Ile
                500                 505                 510

Tyr Ser Leu Val Leu Lys Lys Asn Val Pro Phe Thr Tyr Glu Ile Leu
            515                 520                 525

Leu Asn Ile Leu Asn Ser Pro Leu Tyr Glu Pro Tyr Phe Lys Thr Phe
            530                 535                 540

Ala Lys Lys Leu Gly Glu Asn Leu Tyr Glu Tyr Tyr Pro Asn Asn Leu
545                 550                 555                 560

Met Lys Leu Cys Ile Pro Ser Ile Asp Phe Gly Gly Glu Asn Asn Ile
                565                 570                 575

Glu Lys Lys Leu Tyr Asp Phe Phe Gly Leu Thr Asp Lys Glu Ile Glu
                580                 585                 590

Ile Val Glu Lys Ile Lys Asp Asn Cys
595                 600

<210> SEQ ID NO 8
<211> LENGTH: 1806
<212> TYPE: DNA
<213> ORGANISM: Artificial Sequence
<220> FEATURE:
<223> OTHER INFORMATION: designed type II methyltransferase

<400> SEQUENCE: 8
atgtttccgt gcaatgccta tatcgaatat ggtgataaaa atatgaacag ctttatcgaa      60
gatgtggaac agatctacaa cttcattaaa aagaacattg atgtggaaga aaagatgcat     120
ttcattgaaa cctataaaca gaaaagcaac atgaagaaag agattagctt tagcgaagaa     180
tactataaac agaagattat gaacggcaaa aatggcgttg tgtacacccc gccggaaatg     240
gcggccttta tggttaaaaa tctgatcaac gttaacgatg ttattggcaa tccgtttatt     300
aaaatcattg acccgagctg cggtagcggc aatctgattt gcaaatgttt tctgtatctg     360
aatcgcatct ttattaagaa cattgaggtg attaacagca aaaataacct gaatctgaaa     420
ctggaagaca tcagctacca catcgttcgc aacaatctgt ttggcttcga tattgacgaa     480
accgcgatca aagtgctgaa aattgatctg tttctgatca gcaaccaatt tagcgagaaa     540
aatttccagg ttaaagactt tctggtggaa atattgatc gcaaatatga cgtgttcatt     600
ggtaatccgc gtatatcgg tcacaaaagc gtggacagca gctacagcta cgtgctgcgc     660
aaaatctacg gcagcatcta ccgcgacaaa ggcgatatca gctattgttt ctttcagaag     720
```

```
agcctgaaat gtctgaagga aggtggcaaa ctggtgtttg tgaccagccg ctacttctgc      780
gagagctgca gcggtaaaga actgcgtaaa ttcctgatcg aaaacacgag catttacaag      840
atcattgatt tttacggcat ccgcccgttc aaacgcgtgg gtatcgatcc gatgattatt      900
tttctggttc gtacgaagaa ctggaacaat aacattgaaa ttattcgccc gaacaagatt      960 gaaagaacg aaaagaacaa attcctggat agcctgttcc tggacaaaag cgaaaagtgt     1020
aaaaagttta gcattagcca gaaaagcatt aataacgatg ctgggttttt cgtggacgaa     1080
gtggagaaaa acattatcga caaatcaaa gagaaaagca gttcattct gaaagatatt       1140 tgccatagct gtcaaggcat tatcaccggt tgtgatcgcg cctttattgt ggaccgtgat     1200
atcatcaata gccgtaagat cgaactgcgt ctgattaaac cgtggattaa aagcagccat     1260
atccgtaaga tgaagttat taagggcgaa aaattcatca tctatagcaa cctgattgag      1320
aatgaaaccg agtgtccgaa tgcgattaaa tatatcgaac agtacaagaa acgtctgatg     1380
gagcgccgcg aatgcaaaaa gggcacgcgt aagtggtatg aactgcaatg gggccgtaaa     1440
ccggaaatct tcgaagaaaa gaaaattgtt ttcccgtata aaagctgtga caatcgtttt     1500
gcactggata agggtagcta ttttagcgca gacattata gcctggttct gaagaaaaat      1560
gtgccgttca cctatgagat cctgctgaat atcctgaata gcccgctgta cgagttttac     1620
tttaagacct tcgcgaaaaa gctgggcgag atctgtacg agtactatcc gaacaacctg       1680
atgaagctgt gcatcccgag catcgatttc ggcggtgaga acaatattga gaaaagctg       1740 tatgatttct ttggtctgac ggataaagaa attgagattg tggagaagat caagataac     1800 tgctaa                                                                 1806
```

<210> SEQ ID NO 9
<211> LENGTH: 61
<212> TYPE: PRT
<213> ORGANISM: Clostridium autoethanogenum

<400> SEQUENCE: 9

Cys Lys Lys Asn Pro Ile Ser Glu Leu Ala Asn Ser Ile Asn Glu Val
 1               5                  10                  15

Gly Asp Met Lys Gly Leu Thr Pro Glu Thr Ile Leu Lys Val Ile Glu
            20                  25                  30

Lys Leu Leu Ser Glu Glu Lys Lys Thr Ser Leu Glu Gly Leu Glu Pro
        35                  40                  45

Gly Lys Asp Ile Asn Leu Gly Ser Tyr Gly Asn Lys Glu
    50                  55                  60

<210> SEQ ID NO 10
<211> LENGTH: 28
<212> TYPE: DNA
<213> ORGANISM: Artificial Sequence
<220> FEATURE:
<223> OTHER INFORMATION: oligonucleotide Ppta-ack-NotI-F

<400> SEQUENCE: 10
gagcggccgc aatatgatat ttatgtcc                                          28

<210> SEQ ID NO 11
<211> LENGTH: 28
<212> TYPE: DNA
<213> ORGANISM: Artificial Sequence
<220> FEATURE:
<223> OTHER INFORMATION: oligonucleotide Ppta-ack-NdeI-R

<400> SEQUENCE: 11
ttccatatgt tcatgttca tttcctcc                                         28

<210> SEQ ID NO 12
<211> LENGTH: 2941
<212> TYPE: DNA
<213> ORGANISM: Artificial Sequence
<220> FEATURE:
<223> OTHER INFORMATION: codon optimized pddABD operon

<400> SEQUENCE: 12

```
catatgagat cgaaaagatt tgaagcactg gcgaaacgcc ctgtgaatca ggacggcttc      60
gttaaggagt ggatcgaaga aggctttatc gcgatggaaa gcccgaacga cccaaaaccg     120
tcgattaaaa tcgttaacgg cgcggtgacc gagctggacg ggaaaccggt aagcgatttt     180
gacctgatcg accactttat cgcccgctac ggtatcaacc tgaaccgcgc cgaagaagtg     240
atggcgatgg attcggtcaa gctgccaaac atgctgtgcg atccgaacgt taaacgcagc     300
gaaatcgtcc cgctgaccac cgcgatgacg ccggcgaaaa ttgtcgaagt ggtttcgcat     360
atgaacgtcg tcgagatgat gatggcgatg cagaaaatgc gcgcccgccg cacccccgtcc    420
cagcaggcgc acgtcaccaa cgtcaaagat aacccggtac agattgccgc cgacgccgcc    480
gaagggggcat ggcgcggatt tgacgaacag gaaaccaccg ttgcggtagc gcgctatgcg   540
ccgttcaacg ccatcgcgct gctggtgggc tcgcaggtag gccgtccggg cgtgctgacg    600
cagtgctcgc tggaagaagc caccgagctg aagctcggca tgctgggcca cacctgctac    660
gccgaaacca tctccgtcta cggcaccgag ccggtcttta ccgacggcga cgacacgccg    720
tggtcgaagg gcttcctcgc ctcgtcctac gcctctcgcg ggctgaaaat gcgcttttacc   780
tccggctccg gtcggaagt gcagatgggc tacgccgaag gcaaatccat gctttatctg    840
gaagcgcgct gcatctacat caccaaagcc gcgggcgtac agggtctgca aaacggttcc   900
gtaagctgca tcggcgtgcc gtctgcgtg ccttccggca ttcgcgcggt gctggcggaa    960
aacctgatct gttcgtcgct ggatctggag tgcgcctcca gcaacgacca gaccttcacc    1020
cactccgata tgcgtcgtac cgcgcgcctg ctgatgcagt tcctgccggg caccgacttt    1080
atctcctccg gttattccgc ggtgccgaac tacgacaaca tgttcgccgg ctccaacgaa    1140
gatgccgaag acttttgacga ctacaacgtc atccagcgcg acctgaaggt ggacggcggt    1200
tgcgtccgg ttcgcgaaga ggacgtcatc gccatccgta caaagccgc ccgcgcgctg      1260
caggccgtgt ttgccggaat ggggctgccg ccgattaccg atgaagaagt tgaagccgcg    1320
acctacgccc acggttcgaa agatatgccg gagcgcaaca tcgtcgaaga catcaagttc    1380
gcccaggaaa tcatcaataa aaaccgcaac ggtctggaag tggtgaaagc gctggcgcag    1440
ggcggattca ccgacgtggc ccaggacatg ctcaacatcc agaaagctaa gctgaccggg    1500
gactacctgc ataccctgcg gattatcgtc ggcgacgggc aggtgctgtc agccgtcaac    1560
gacgtcaacg actatgccgg tccggcaacg ggctatcgcc tgcagggcga acgctgggaa    1620
gagattaaaa acatccctgg cgctcttgat cccaacgaga ttgattaaaa aaaaaaaaaa    1680
aaaaaaaaaa aaaaaaaaaa aaaatggaaa ttaatgaaaa attgctgcgc cagataattg    1740
aagacgtgct cagcgagatg aagggcagcg ataaaccggt ctcgtttaat gcgccggcgg    1800
cctccgcggc gccccaggcc acgcgcccg ccggcgacgg cttcctgacg gaagtgggcg     1860
aagcgcgtca gggaacccag caggacgaag tgattatcgc cgtcggcccg gctttcggcc    1920
tggcgcagac cgtcaatatc gtcggcatcc cgcataagag cattttgcgc gaagtcattg    1980
```

```
ccggtattga agaagaaggc attaaggcgc gcgtgattcg ctgctttaaa tcctccgacg    2040
tggccttcgt cgccgttgaa ggtaatcgcc tgagcggctc cggcatctct atcggcatcc    2100
agtcgaaagg caccacggtg atccaccagc aggggctgcc gccgctctct aacctggagc    2160
tgttcccgca ggcgccgctg ctgaccctgg aaacctatcg ccagatcggc aaaaacgccg    2220
cccgctatgc gaaacgcgaa tcgccgcagc cggtcccgac gctgaatgac cagatggcgc    2280
ggccgaagta ccaggcgaaa tcggccattt tgcacattaa agagaccaag tacgtggtga    2340
cgggcaaaaa cccgcaggaa ctgcgcgtgg cgctttgaaa aaaaaaaaa aaaaaaaaa     2400 aaaaaaaaa aaaatgaata ccgacgcaat tgaatcgatg gtacgcgacg tattgagccg    2460
catgaacagc ctgcagggcg aggcgcctgc ggcggctccg gcggctggcg gcgcgtcccg    2520
tagcgccagg gtcagcgact acccgctggc gaacaagcac ccggaatggg tgaaaaccgc    2580
caccaataaa acgctggacg actttacgct ggaaaacgtg ctgagcaata aagtcaccgc    2640
ccaggatatg cgtattaccc cggaaaccct gcgcttacag gcttctattg ccaaagacgc    2700
gggccgcgac cggctggcga tgaacttcga gcgcgccgcc gagctgaccg cggtaccgga    2760
cgatcgcatt cttgaaatct acaacgccct ccgcccctat cgctcgacga agaggagct    2820 gctggcgatc gccgacgatc tcgaaagccg ctatcaggcg aagatttgcg ccgctttcgt    2880
tcgcgaagcg gccacgctgt acgtcgagcg taaaaaactc aaaggcgacg attaagaatt    2940
c                                                                  2941

<210> SEQ ID NO 13
<211> LENGTH: 344
<212> TYPE: DNA
<213> ORGANISM: Artificial Sequence
<220> FEATURE:
<223> OTHER INFORMATION: intron targeting region for diol dehydratase

<400> SEQUENCE: 13
aagcttataa ttatccttac gagacgccgc agtgcgccca gatagggtgt taagtcaagt      60
agtttaaggt actactctgt aagataacac agaaacagc caacctaacc gaaaagcgaa     120
agctgatacg ggaacagagc acggttggaa agcgatgagt tacctaaaga caatcgggta     180
cgactgagtc gcaatgttaa tcagatataa ggtataagtt gtgtttactg aacgcaagtt     240
tctaatttcg gtttctcgtc gatagaggaa agtgtctgaa acctctagta caaagaaagg     300
taagttaaat gcggcgactt atctgttatc accacatttg taca                     344

<210> SEQ ID NO 14
<211> LENGTH: 25
<212> TYPE: DNA
<213> ORGANISM: Artificial Sequence
<220> FEATURE:
<223> OTHER INFORMATION: oligonucleotide Og84f

<400> SEQUENCE: 14
aaacctcatt agaaggattg gagcc                                             25

<210> SEQ ID NO 15
<211> LENGTH: 25
<212> TYPE: DNA
<213> ORGANISM: Artificial Sequence
<220> FEATURE:
<223> OTHER INFORMATION: oligonucleotide Og85r

<400> SEQUENCE: 15
gaaactggtg atacaccatc tgcta                                             25
```

-continued

```
<210> SEQ ID NO 16
<211> LENGTH: 37
<212> TYPE: DNA
<213> ORGANISM: Artificial Sequence
<220> FEATURE:
<223> OTHER INFORMATION: oligonucleotide fD1

<400> SEQUENCE: 16
ccgaattcgt cgacaacaga gtttgatcct ggctcag                              37

<210> SEQ ID NO 17
<211> LENGTH: 37
<212> TYPE: DNA
<213> ORGANISM: Artificial Sequence
<220> FEATURE:
<223> OTHER INFORMATION: oligonucleotide rP2

<400> SEQUENCE: 17
cccgggatcc aagcttacgg ctaccttgtt acgactt                              37

<210> SEQ ID NO 18
<211> LENGTH: 684
<212> TYPE: DNA
<213> ORGANISM: Clostridium autoethanogenum

<400> SEQUENCE: 18
cgggcrraww twaatttagg tagttatgga aataaagaga gtattcgtca aatgctatta     60
aatagagcac ctaagtttgg taatgatata gatgaggttg atgatttagc acgagaagcc    120
gcagtgcgcc cagatagggt gttaagtcaa gtagtttaag gtactactct gtaagataac    180
acagaaaaca gccaacctaa ccgaaaagcg aaagctgata cgggaacaga gcacggttgg    240
aaagcgatga gttacctaaa gacaatcggg tacgactgag tcgcaatgtt aatcagatat    300
aaggtataag ttgtgtttac tgaacgcaag tttctaattt cggtttctcg tcgatagagg    360
aaagtgtctg aaacctctag tacaaagaaa ggtaagttaa atgcggcgac ttatctgtta    420
tcaccacatt tgtacaatct gtaggagaac ctatgggaac gaaacgaaag cgatgccgag    480
aatctgaatt taccawgact taacactaac tggggatacc ctaaacaaga atgcctaata    540
kaaaggagga aaaaggctat agcactagag cttgaaaatc ttgcaagggt acggagtact    600
cgtaktagtc tgagwagggt aacgcccttt acatggmaar ggggtamwgt wawwgtktyc    660
twraattwaa wattrawtag ykat                                            684

<210> SEQ ID NO 19
<211> LENGTH: 1124
<212> TYPE: DNA
<213> ORGANISM: Clostridium autoethanogenum

<400> SEQUENCE: 19
tyttttcaat ctwggtgttg ctcctgtctg tgatcccatt ggaacatttg cagaaacagg     60
ataaagtcct ggttggaatt gaccattacg tggattagtg tatttttcaa cttcattaca    120
gtaaattaag tgaagtaggg aggtaccgcc ttgttcacat tactgtgact ggtttgcacc    180
accctcttcg ggaaccgtac gtaccgctct cggagtatac ggctctgtta ttgttcgttc    240
gtaaaaattc actgtcgaca ttcacttgtg tttatgaatc acgtgacgat gacaatgaaa    300
gcatacaaca agagttttac gttgtttcgc tatcattgcc atttcccaac gcgtgaagtt    360
cctattctct agaagtata ggaacttcta tattgataaa ataataata gtgggtaaa      420 ttaagttgtt agagaaaacg tataaattag gagggattca tatggaccca agagatgctg    480
```

| | |
|---|---|
| gtgcttctgg tgctggtatg aacaaaaata taaaatattc tcaaaacttt ttaacgagtg | 540 |
| aaaaagtact caaccaaata ataaaacaat tgaatttaaa agaaaccgat accgtttacg | 600 |
| aaattggaac aggtaaaggg catttaacga cgaaactggc taaaataagt aaacaggtaa | 660 |
| cgtctattga attagacagt catctattca acttatcgtc agaaaaatta aaactgaata | 720 |
| ctcgtgtcac tttaattcac caagatattc tacagtttca attccctaac aaacagaggt | 780 |
| ataaaattgt tgggagtatt ccttaccatt taagcacaca aattattaaa aaagtggttt | 840 |
| tgaaagccat gcgtctgaca tctatctgat tgttgaagaa ggattctaca agcgtmyttg | 900 |
| gwtattcacc raacwctakg gttgctcttg cacactcagt ctcgattyac aattgcttaa | 960 |
| gctgccwscg aatgctttcw cctaaacaaa ktaammgtgt cttataawac ttwcccscwt | 1020 |
| aycacwgatg ttccarataa awtggaakct attacgtact tgttcaaatg kgtcatcaar | 1080 |
| mywckcatsg tamtaaaatcr tytmwcagca tgmacrscma kkaa | 1124 |

<210> SEQ ID NO 20
<211> LENGTH: 1279
<212> TYPE: DNA
<213> ORGANISM: Clostridium autoethanogenum

<400> SEQUENCE: 20

| | |
|---|---|
| cggggcarra awtwatttag gtagttatgg aaataaagag agtattcgtc aaatgctatt | 60 |
| aaatagagca cctaagtttg gtaatgatat agatgaggtt gatgatttag cacgagaagc | 120 |
| cgcagtgcgc ccagataggg tgttaagtca agtagtttaa ggtactactc tgtaagataa | 180 |
| cacagaaaac agccaaccta accgaaaagc gaaagctgat acgggaacag agcacggttg | 240 |
| gaaagcgatg agttacctaa agacaatcgg gtacgactga gtcgcaatgt taatcagata | 300 |
| taaggtataa gttgtgttta ctgaacgcaa gtttctaatt tcggtttctc gtcgatagag | 360 |
| gaaagtgtct gaaacctcta gtacaaagaa aggtaagtta aatgcggcga cttatctgtt | 420 |
| atcaccacat ttgtacaatc tgtaggagaa cctatgggaa cgaaacgaaa gcgatgccga | 480 |
| gaatctgaat ttaccaagac ttaacactaa ctggggatac cctaaacaag aatgcctaat | 540 |
| agaaaggagg aaaaaggcta tagcactaga gcttgaaaat cttgcaaggg tacggagtac | 600 |
| tcgtagtagt ctgagaaggg taacgcccct tacatggcaa aggggtacag ttattgtgta | 660 |
| ctaaaattaa aaattgatta gggaggaaaa cctcaaaatg aaaccaacaa tggcaatttt | 720 |
| agaaagaatc agtaaaaatt cacaagaaaa tatagacgaa gtttttacaa gactttatcg | 780 |
| ttatctttta cgtccagata tttattacgt ggcgacgcgt gaagttccta tactttctag | 840 |
| agaataggaa cttcgcgact catagaatta tttcctcccg ttaaataata gataactatt | 900 |
| aaaaatagac aatacttgct cataagtaac ggtacttaaa ttgtttactt tggcgtgttt | 960 |
| cattgcttga tgaaactgat tttagtaaac agttgacgat atctcgattg acccatttga | 1020 |
| aacaaagtac gtatatagct tcatatttat ctgaacatct gtggtatggc ggtagtttat | 1080 |
| agacctgtta ctttggttta gatgaagcat cgctgcagct agcatgctga tcgagactga | 1140 |
| kkkcaagaca cctatgttcg kgaawtcagt asctkgatcy tctcmmmacw cratwaagtc | 1200 |
| arcatggctt cgaacactta gaatttggty twwgkgagat tcgaataacc gtgtgttaga | 1260 |
| aktacytsaa aacctctga | 1279 |

<210> SEQ ID NO 21
<211> LENGTH: 1297
<212> TYPE: DNA
<213> ORGANISM: Clostridium autoethanogenum

<400> SEQUENCE: 21

```
aggggggtyag ctttttcttc atctggtgtt gctcctgtct gtgatcccat tggaacattt       60
gcagaaacag gataaagtcc tggttggaat tgaccattac gtggattagt gtatttttca      120
acttcattac agtaaattaa gtgaagtagg gaggtaccgc cttgttcaca ttactgtgac      180
tggtttgcac caccctcttc gggaaccgta cgtacccctc tcggagtata cggctctgtt      240
attgttcgtt cgtaaaaatt cactgtcgac attcacttgt gtttatgaat cacgtgacga      300
tgacaatgaa agcatacaac aagagtttta cgttgtttcg ctatcattgc catttcccaa      360
cgcgtgaagt tcctattctc tagaaagtat aggaacttct atattgataa aaataataat      420
agtgggtata attaagttgt tagagaaaac gtataaatta ggagggattc atatggaccc      480
aagagatgct ggtgcttctg gtgctggtat gaacaaaaat ataaaatatt ctcaaaactt      540
tttaacgagt gaaaaagtac tcaaccaaat aataaaacaa ttgaatttaa agaaaccga      600
taccgtttac gaaattggaa caggtaaagg gcatttaacg acgaaactgg ctaaaataag      660
taaacaggta acgtctattg aattagacag tcatctattc aacttatcgt cagaaaaatt      720
aaaactgaat actcgtgtca ctttaattca ccaagatatt ctacagtttc aattccctaa      780
caaacagagg tataaaattg ttgggagtat tccttaccat ttaagcacac aaattattaa      840
aaaagtggtt tttgaaagcc atgcgtctga catctatctg attgttgaag aaggwttcta      900
caagcgtacc ttggatattc accgaacact agggttgctc ttgcacactc aagtctcgat      960
tcagcaattg cttaagctgc cagcggaatg ctttcatcct aaaccaaagt aaacagtgtc     1020
tataaactta cccgcatacc acagatgttc cagataatat tggagctata tacgtacttt     1080
gttcaaatgg tcatcgagaa tatcgtcact gttactaaaa tcagttcatc agcatgaamm     1140
gccagtaaca ttagtacgtt acttatgrca rgwttgcyat tttaagtwtc twtawtacgg     1200
gagaatattc wgagtcsgag ttctattyct gagwtgactc acgtkcgcag ataaaatckg     1260
acctagarac gtataggact ttgactataa ctsctgc                             1297
```

<210> SEQ ID NO 22
<211> LENGTH: 754
<212> TYPE: DNA
<213> ORGANISM: Clostridium autoethanogenum

<400> SEQUENCE: 22

```
cgggcasagc ctwacaymtk asaakycska wsmmggkasc cgtaagcttg gatcccggga     60
ygacgggtga gtaacmsgkg ggtraccwac sycrrrgagg gggatagcct cccsaawggg    120
akattaatac cscataataw tcagttttcw catggagact gatttaaagg agtaatccgy    180
tttgagatgg acccgcggcg cattagctwk ttggtagggt aacggcctac caaggcgack    240
atgcgtagcc gacctgasag ggtgatcggc cacattggaa ctgasagacg gyccasactc    300
ctacgggagg cascagtggg gaatattgca caatgggcga aagcctgatg cagcaacgcc    360
gcgtgagtga agaaggtttt cgrattgtaa agctctgtct ttggggacga taatgacggt    420
accsaaggag gaagccmcgg staactacgk gccascagcc kcggtaatac rtaggtggcg    480
agcgttgtcc ggaattactg ggcgtaaaga gtgcgtakgc ggatatttaa gtgagakgtg    540
raatacccgg gcttaacccg ggywctgywt ttcamaykgg atatcwakag tgcgggagag    600
gagawtggaa ktccwagkgt agcggtgaar tgcgtarasa tymgraasaa maycwktwkc    660
gwwkgcgatt ctcwgkaccr trrytgayrc tgaggytcga aascgtgggt akcaaacwgm    720
attawatacy ctggtastcc acsyygtwaa cgtg                                754
```

<210> SEQ ID NO 23
<211> LENGTH: 885
<212> TYPE: DNA
<213> ORGANISM: Clostridium autoethanogenum

<400> SEQUENCE: 23

```
cattagggcc stcskacycc kwagyccrwc kragccrgga tcaarcmctg ttgtcgacka      60
attcggrctm tcatggwtsw racksgskkk gygwacaagg cccgggaacg tattcaccgc     120
gacattctga ttcgcgatta ctagcaactc caacttcatg taggcgagtt tcagcctgca     180
atccgaactg ggggcagttt ttgaggtttg ctccaccttg cggtcttgct tctctctgta     240
ctgcccattg tagcacgtgt gttgccctgg acataagggg catgatgatt tgacgtcatc     300
cccaccttcc tccgcgttaa ccgcggcagt cttgctagag tgctcaayta awtgttagca     360
actaacaaca ggggttgcgc tcgttgcagg acttaaccta acatctcacg acacgagctg     420
acgacaaccw tgcaccacct gtwtccctgc cccgaagggy ttctcttatc tctaagatat     480
tcagggtatg tcaagtccag gtaaggttct tcgcgttgct tcraattaaa ccacatgctc     540
cgctgcttgt gcgggccccc gtcaattcct ttgagtttta atcttgcgat cgtacttccc     600
aggcggagta cttattgtgt twactgcgkc acaraaggrg tcgatacctc ctacayctag     660
tactcatcgt ttacggcgtg kactaccakg gtatctaatc ctgtttgctm cccaykcttt     720
cktgccwcak cgtcwrttac rktcmaakaa tcsccttygc cwctggtgtt ttccwaatct     780
ctaskkwtty ackgsamwyt agsaattcct tytcctcycc cgymcyctar atatccyrtt     840
tgaatgcagt gmcmwgrtaa mcccggkatt mmawctytmt taatt                    885
```

<210> SEQ ID NO 24
<211> LENGTH: 1005
<212> TYPE: DNA
<213> ORGANISM: Clostridium autoethanogenum

<400> SEQUENCE: 24

```
agcagggcar gcctwacacm tkasaakycs krwssmggka gccgtaagct tggatcccgg      60
gaygacgggt gagtaacrsg kgggtraccw acsycrrrga gggggatagc ctcccsaawg     120
ggakattaat accscataat aatcagtttt cwcatggaga ctgwtttaaa ggagtaatcc     180
gyttgagat ggacccgcgg cgcattagct wkttggtagg gtaacggcct accmaggcga     240
ckatgcgtag ccgacctgas agggtgatcg gccacwttgg aactgasaga ckgtccasac     300
tcctacggga ggcagcagtg gggaatattg cacaakgggc gaaagcctga tgcascaacg     360
ccgcgtgagt gaagaaggtt ttcggattgt aaagctctgt ctttggggac gatratgacg     420
gtaccsaagg aggargccmc ggstaactac gkgccascmk ccgcggtaat acgtasgtgg     480
cgagcgttgt ccggaattac tgggcgtaaa gagtgcgtag gcggatattt aagtgagatg     540
tgaaataccc gggcttaacc ygggywctgc atttcaaact ggatatctag agtgcgggag     600
aggagaatgg aattcctagt gtagcggtga atgcgtaka sattakgaag aacaccaktg     660
gcgaaggcga ttytctggac cgtractgay gctgakgcac gaaagcgtgg gtakcaaaca     720
ggattagata cyctggtagt ccacrccgta aacgatgagt actkggtgta ggaggtwtcg     780
accccttmtg tgccgcakta aacacwataa ktactccgcc tggaawgtac gatcgcaakw     840
twaaawctca arggakttga cggggcscg cwcwagcakc ggagcawgtk gkttaattys     900
arcwcgyraa samcttacct ggamytkacw wmcctkmatw yttwaraswt agwgyrscct     960
tsrggsaggg awrrwkksgt gtrtgttsck cakwycgtyt rtaag                    1005
```

<210> SEQ ID NO 25
<211> LENGTH: 1117
<212> TYPE: DNA
<213> ORGANISM: Clostridium autoethanogenum

<400> SEQUENCE: 25

| | | | | | |
|---|---|---|---|---|---|
| cccgcwgycr | tagcykyskm | kwckwagkyr | wckragmcrr | gatcaarctc | tgttgtcgac | 60 |
| raattcggac | tmtcakggtg | wgacgggsgg | kgtgwacaak | gcccgggaac | gtattcaccg | 120 |
| cgacattctg | attcgcgatt | actagcaact | ccaacttcat | gtaggcgagt | ttcagcctgc | 180 |
| aatccgaact | gggggcagtt | tttgaggttt | gctccacctt | gcggtcttgc | ttctctctgt | 240 |
| actgcccatt | gtagcacgtg | tgttgccctg | gacataaggg | gcatgatgat | ttgacgtcat | 300 |
| ccccaccttc | ctccgcgtta | accgcggcag | tcttgctaga | gtgctcaact | aaatgttagc | 360 |
| aactaacaac | aggggttgcg | ctcgttgcag | gacttaacct | aacatctcac | gacacgagct | 420 |
| gacgacaacc | atgcaccacc | tgtatccctg | ccccgaaggg | yttctcttat | ctctaarata | 480 |
| ttcagggtat | gtcaagtcca | ggtaaggttc | ttcgcgttgc | ttcraattaa | accacatgct | 540 |
| ccgctgcttg | tgcgggcccc | cgtcaattcc | tttgagtttt | aatcttgcga | tcgtacttcc | 600 |
| caggcggagt | acttattgtg | tttactgcgg | cacagaaggg | gtcgatacct | cytacaccta | 660 |
| gtactcatcg | tttacggcgt | ggactaccag | ggtatctaat | cctgtttgct | acccacgctt | 720 |
| tcgtgcctca | kcgtcagtta | cggtccagag | aatcgccttc | gccactggtg | ttcttcctaa | 780 |
| tctctacgca | tttmaccgct | acactaggaw | tycmttctcc | tctcccgcac | tctagatatc | 840 |
| yagtttkaaa | tgcagtgccc | gggttaagcc | cgggtatttc | acatctcact | waatatccgc | 900 |
| ctacgcactc | kttmcgccca | gtaatyccga | macgctcgcm | yctacgtatt | acgcggytgc | 960 |
| tgcacgtagt | tagccgkgct | tyctcttggg | tmccgtmmtt | ayskycccaa | kamagagctt | 1020 |
| tacaatckga | aacyttcttm | wytcmksmgs | gtgctgmtag | cttygycwtg | kgcaawatcc | 1080 |
| mmtgcgccyy | cgatgakytg | rwctgyctma | ktyaagt | | | 1117 |

<210> SEQ ID NO 26
<211> LENGTH: 3566
<212> TYPE: DNA
<213> ORGANISM: Artificial Sequence
<220> FEATURE:
<223> OTHER INFORMATION: C. autoethanogenum diol dehydratase operon
      codon optimized for E. coli

<400> SEQUENCE: 26

| | | | | | |
|---|---|---|---|---|---|
| atttcacaca | ggaaacagac | catgaatgac | gtgctgaata | aactgtatac | cgccaatcag | 60 |
| agcaaacgca | ttgaaaaact | gaccaacgat | ctgtatagcg | tgacaccgga | aattgaagca | 120 |
| cagcgtgcag | ttctgattac | cgaaagcttt | aaagaaaccg | aagcctaccc | gatgattatt | 180 |
| cgtcgtgcaa | aagcactgga | aaaaatcctg | aacgaaatgg | atattgtgat | ccgtgatgaa | 240 |
| gaactgattg | ttggcaatct | gaccaaaaaa | ccgcgtgcag | caagcatttt | tccggaattt | 300 |
| agcaataaat | ggctgctgga | agaatttgat | accctgcaa | aacgtaccgg | tgatgttttt | 360 |
| ctgattagcg | aggatgttaa | aagccagctg | cgtgaagttt | tcaaatattg | ggatggtaaa | 420 |
| accaccaatg | aactggcaac | cgaatatatg | tttagcgaaa | ccaaagaagc | aatgaaagca | 480 |
| ggcgttttta | ccgttggcaa | ctattatttc | aatggcattg | gtcatatcag | cgtggattat | 540 |
| gcaaaagttc | tgagcaaagg | ctttaacggc | attattgaag | atgccgaaag | cgaaaaagca | 600 |
| aaagcagata | agccgatcc | ggattatatc | aaaaaagatc | agtttctgac | cgcagtgatc | 660 |
| attaccagca | aagccgttat | caaatttgca | cgtcgttttg | cagaactggc | acgtaatctg | 720 |

```
gcaagccaga gcctggatag ccgtcgtcgt gaggaactga tgcagattgc agaaaattgt      780
cagtgggtgc cggaacgtcc tgcacgtacc ttttatgaag cactgcagag cttttggttt      840
gtgcagagca ttattcagat tgaaagcaac ggtcatagca ttagcccgat gcgttttgat      900
cagtatatgt acccgtactt caaaaaagac gttagcaatg gtctgatcac ccaagaaaaa      960
gcacaagaac tgctggattg tctgtgggtc aaattcaatg atgtgaacaa agttcgtgat     1020
gagggtagca ccaaagcatt tggcggttat ccgatgtttc agaatctgat tgtgggtggc     1080
cagacaattg atggtcgtga tgcaacaaat gaactgagct ttatgtgtct ggaagcaacc     1140
gcacatacca aactgccgca gccgagcatt agcattcgtg catggaataa acaccggat      1200
gaactgctgc tgaaagcagc agaagttacc cgtctgggtc tgggtatgcc tgcctattat     1260
aacgatgaag ttattattcc gagcctgacc agccgtggtc tgaccctgga agatgcacgt     1320
gattatggta ttattggttg tgttgaaccg cagaaaggtg gcaaaaccga aggttggcat     1380
gatgcagcct ttttcaatat tgttaaagtg ctggaaatca ccatcaacaa cggtatggat     1440
aacggtaaac aaattggtct gcgcaccggt gattttacca gctttaccag ttttgagaaa     1500
ctgttcgatg cctacaaact gcagatggaa tattttgtga aactgctggt gaatgccgat     1560
aattcagttg atctggcaca tggtaacgt gcaccgctgc cgtttctgag cagcatggca     1620
gatgattgta ttgcacgtgg taaaagcctg caagaaggtg gcgcacatta aactttacc     1680
ggtccgcagg gtgttggtgt tgcaaatgca gcagatagcc tggaagccat caaaaaactg     1740
gtgttcgagg acaaaaaaat caccctgcag gatctgaaaa atgccctgga taccaatttt     1800
ggcgagtgca aaaaaaaccc gattagcgaa ctggccaata gcattaatga agtgggtgat     1860
atgaaaggcc tgactccgga aaccattctg aaagttatcg aaaaactgct gagcgaagag     1920
aaaaaaacca gtctggaagg tctggaaccg ggtaaagata tcaatctggg tagctatggt     1980
aacaaagaaa gcattcgtca gatgctgctg aatcgtgcac cgaaatttgg caatgatatt     2040
gatgaagttg atgacctggc acgtgaagca gcactgattt attgtaacga agtggaaaag     2100
tataccaatc cgcgtaatgg ccagtttcag cctggtctgt atccggttag cgcaaatgtt     2160
ccgatgggta gccagaccgg tgcaactccg gatggtcgta aagccggtga accgctggca     2220
gatggtgtta gtccggtgag tggccgtgat gccatgggtc cgaccgcagc agcaaatagc     2280
gttgcaaaaa ttgatcattg caaagccagc aatggcaccc tgtttaacca gaaatttcat     2340
ccgagcgcac tggaaggcca gacaggtctg cagaatctgt caagcctggt tcgtaccttc     2400
tttgatgaga aaggtctgca tgttcagttt aatgttgtta gccgtgaaac cctgctggat     2460
gcacagaaaa atccggaaaa ttatcgcaat ctggttgttc gtgttgcagg ttatagcgca     2520
cattttacct cactggataa aagcattcag gacgatatta tcaaacgcac cgaacacacc     2580
ttttaaagct ttttatagga ggaaaagtta tgctgaacta ccaggtgaac ctggataaaa     2640
aaggcatcat ctttgatatc cagcgcttta gcgttcatga tggtccgggt attcgtacca     2700
ttgttttttt caaaggttgt ccgctgagct gtcgttggtg tagcaatccg gaatcacagt     2760
gtatggaacc gcaggtaatg tttattccgt caaaatgcat tggctgcaaa aaatgttatg     2820
aggtgtgcag caatggtgcc atcgatttta atctgccgag ccgtgttgat cagaataaat     2880
gtgttaaatg cggcaaatgc gtggaaaatt gttatgccgg tgcactgaat ctggcaggta     2940
atacccgtac cgttaaagag ctgctgctgg aactgaaaaa agacaacatc tattatcgtc     3000
gtagcggtgg tggtattacc ctgagtggtg gtgaagttac cgcacagccg gaatttgcag     3060
aggaactgct gaaaggttgt aaacagaatg gctggcatac cgcaattgaa accgcagcat     3120
```

```
ttaccagcca gagcgttctg gaacgtatgc tgccgtggct ggatctggtt atgctggata    3180
ttaaacatat ggacgccaac aaacacctgg aatataccgg taaaccgaac gaactgatcc    3240
tgcaaaatgc aaaactgatt gcacagtttg gtgttcagct gattatccgt gttccggtga    3300
ttcctggtgt taatagtgat gaaaacaata ttcgtgccac cgccaattt gcaaccagcc    3360 tgaaaagcgt gaaagaactg catctgctgc cgtatcatcg tctgggtgaa aacaaatatg    3420
aatatctggg ccacgattac atcatgaaag gactgcagcc tccgacaaaa gaagaaatca    3480
ataaactgaa agaactggtg gaagaatgcg gtctgatttg taaagtgggt ggcattgatt    3540
aaagcttggc tgttttggcg gatgag                                        3566
```